US010538762B2

(12) United States Patent
Corey et al.

(10) Patent No.: US 10,538,762 B2
(45) Date of Patent: Jan. 21, 2020

(54) ALLELE SELECTIVE INHIBITION OF MUTANT C9ORF72 FOCI EXPRESSION BY DUPLEX RNAS TARGETING THE EXPANDED HEXANUCLEOTIDE REPEAT

(71) Applicant: The Board of Regents of the University of Texas System, Austin, TX (US)

(72) Inventors: David Corey, Dallas, TX (US); Jiaxin Hu, Coppell, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/518,824

(22) PCT Filed: Oct. 8, 2015

(86) PCT No.: PCT/US2015/054594
§ 371 (c)(1),
(2) Date: Apr. 13, 2017

(87) PCT Pub. No.: WO2016/060919
PCT Pub. Date: Apr. 21, 2016

(65) Prior Publication Data
US 2017/0233735 A1    Aug. 17, 2017

Related U.S. Application Data

(60) Provisional application No. 62/063,548, filed on Oct. 14, 2014.

(51) Int. Cl.
C07H 21/04    (2006.01)
C12N 15/113   (2010.01)
A61K 31/713   (2006.01)

(52) U.S. Cl.
CPC .......... *C12N 15/113* (2013.01); *A61K 31/713* (2013.01); *C12N 2310/14* (2013.01); *C12N 2310/3231* (2013.01); *C12N 2320/34* (2013.01)

(58) Field of Classification Search
None
See application file for complete search history.

(56) References Cited

U.S. PATENT DOCUMENTS

| 7,056,704 B2 * | 6/2006 | Tuschl | A61K 48/00 435/91.1 |
| 7,250,496 B2 | 7/2007 | Bentwich | |
| 2004/0224893 A1 * | 11/2004 | Wang | A61K 38/1793 424/158.1 |
| 2015/0259679 A1 * | 9/2015 | Bennett | C12N 15/113 514/44 A |

FOREIGN PATENT DOCUMENTS

| WO | WO 2013/041577 | 3/2013 |
| WO | WO 2013/162363 | 10/2013 |
| WO | WO 2014/062691 | 4/2014 |

OTHER PUBLICATIONS

Vickers et al. (The Journal of Biological Chemistry, 2003, 278:7108-7118).*
Vickers et al. (The Journal of Biological Chemistry, vol. 278, No. 9, 2003, pp. 7108-7118).*
Paternak et al. (Organic & Bio Chem 2011: 3591-3597).*
DeJesus-Hernandez et al., "Expanded GGGGCC hexanucleotide repeat in noncoding region of C9ORF72 causes chromosome 9p-linked FTD and ALS," *Neuron*, 72:245-256, 2012.
Donnelly et al., "RNA toxicity from the ALS/FTD C9ORF72 expansion is mitigated by antisense intervention," *Neuron*, 80:415-428, 2013.
Fiszer et al., "Inhibition of mutant huntingtin expression by RNA duplex targeting expanded CAG repeats," *Nucleic Acids Res.*, 39:5578-5585, 2011.
Gendron et al., "Antisense transcripts of the expanded C9ORF72 hexanucleotide repeat form nuclear RNA foci and undergo repeat-associated non-ATG translation in c9FTD/ALS," *Acta Neuropathol.*, 126:829-844, 2013.
Hu et al., "Allele-selective inhibition of huntingtin expression by switching to an miRNA-like RNAi mechanism," *Chem. Biol.*, 17:1183-1188, 2010.
Hu et al., "Engineering duplex RNAs for challenging targets: recognition of GGGGCC/CCCCGG repeats at the ALS/FTD C9orf72 locus," *Chem Biol.*, 22:1505-1511, 2015.
Lagier-Tourenne et al., "Targeted degradation of sense and antisense C9orf72 RNA foci as therapy for ALS and frontotemporal degeneration," *Proc. Natl. Acad. Sci. USA*, 110:E4530-E4539, 2013.
Malefyt et al., "Improved asymmetry prediction for short interfering RNAs," *FEBS J.*, 281(1):320-330, 2014.
PCT International Preliminary Report on Patentability issued in International Application No. PCT/US2015/054594, dated Apr. 27, 2017.
PCT International Search Report and Written Opinion issued in International Application No. PCT/US2015/054594, dated Feb. 19, 2016.
Renton et al., "A hexanucleotide repeat expansion in C9ORF72 is the cause of chromosome 9p21-linked ALS-FTD," *Neuron*, 72:257-268, 2011.

(Continued)

*Primary Examiner* — Kimberly Chong
(74) *Attorney, Agent, or Firm* — Parker Highlander PLLC

(57) ABSTRACT

Provided herein are compositions and methods for reducing expression of C9orf72 transcripts in cells containing expanded intronic GGGGCC regions, including those in subjects having or at risk of developing amyotrophic lateral sclerosis (ALS) and frontotemporal dementia (FTD). Provided herein are a double-stranded oligonucleotides of 13 to 22 nucleobases in length targeting a GGGGCC expanded repeat region in an intron of C9orf72, comprises (a) 3-5 central mismatches (within bases 9-14) within a target sequence comprising the expanded repeat sequence, or (h) 3-5 mismatches outside of the seed sequence (bases 2-8 within the guide strand complementary to the expanded repeat sequence).

22 Claims, 4 Drawing Sheets
Specification includes a Sequence Listing.

(56) References Cited

OTHER PUBLICATIONS

Sareen et al., "Targeting RNA foci in iPSC-derived motor neurons from ALS patients with C9ORF72 repeat expansion," *Sci Transl Med.*, 5:208ra149, 2013.
Schwarz et al., "Asymmetry in the assembly of the RNAi enzyme complex," *Cell*, 115:199-208, 2003.
Wang et al., "Structure of an argonaute silencing complex with a seed-containing guide DNA and target RNA duplex," *Nature*, 456:921-926, 2008.
Du et al., "A systematic analysis of the silencing effects of an active siRNA at all single-nucleotide mismatched target sites," *Nucleic Acids Research*, 33(5):1671-1677, 2005.
Filipowicz et al., "Mechanisms of post-transcriptional regulation by microRNAs: are the answers in sight?" *Nat Rev Genet.*, 9(2):102-114, 2008.
Gagnon et al., "RNAi factors are present and active in human cell nuclei," *Cell Reports*, 6(1):211-221, 2014.
Grimson et al., "MicroRNA targeting specificity in mammals: determinants beyond seed pairing," *Molecular Cell*, 27:91-105, 2007.
Knudson and Nielsen, "Antisense properties of duplex- and triplex-forming PNAs," *Nucleic Acids Research*, 24(3):494-500, 1996.
Kurreck, "RNA interference: from basic research to therapeutic applications," *Angew. Chem. Int. Ed.*, 48(8):1378-1398, 2009.
Lennox and Behlke, "Cellular localization of long non-coding RNAs affects silencing by RNAi more than by antisense oligonucleotides," *Nucleic Acids Research*, 44(2):863-877, 2016.
Liu et al., "Argonaute2 is the catalytic engine of mammalian RNAi," *Science*, 305(5689):1437-1441, 2004.
Petri and Meister, "siRNA design principles and off-target effects," *Methods Mol Biol.*, 986:59-71, 2013.

* cited by examiner

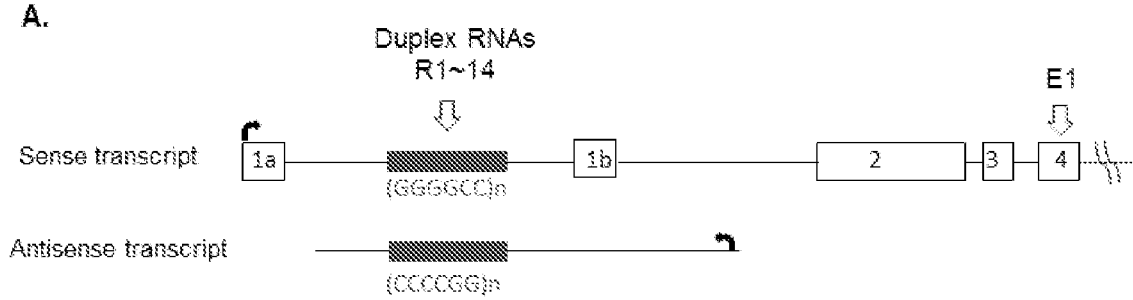
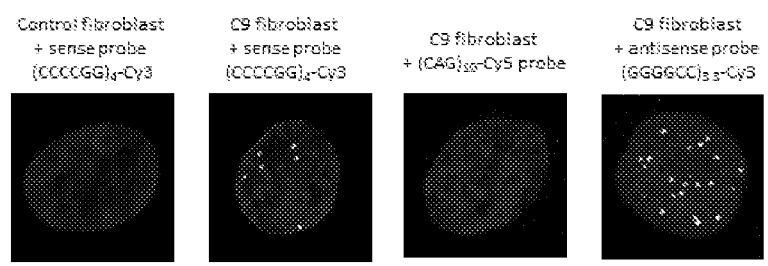
FIGS. 1A-B

A.
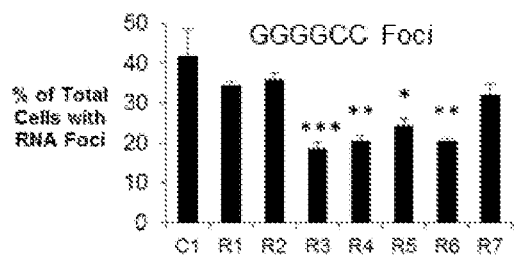 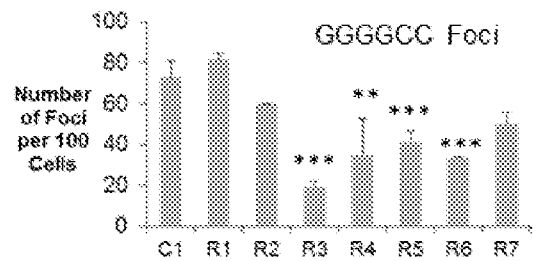
B.
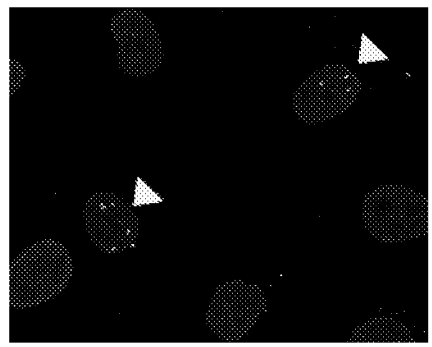 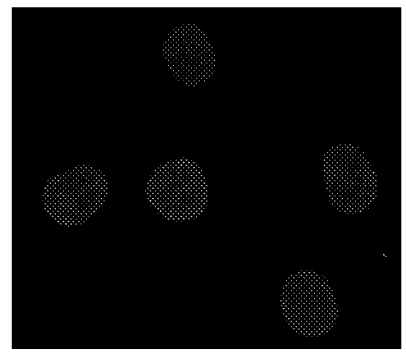
C.
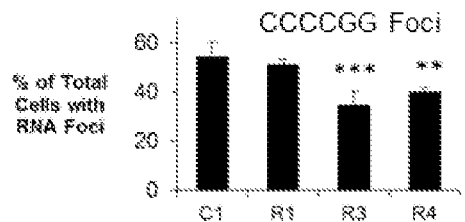 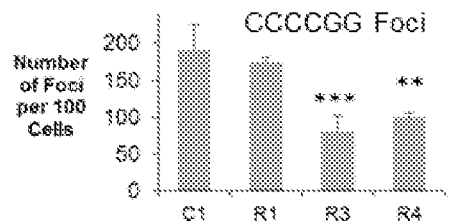
D.
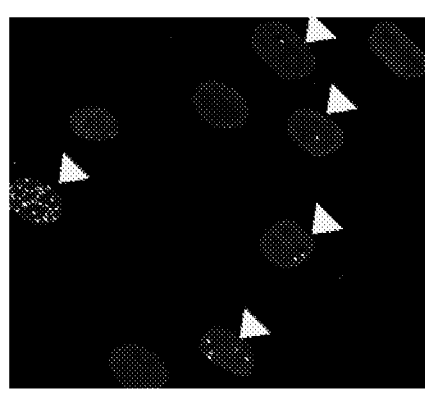 
FIGS. 2A-D A.
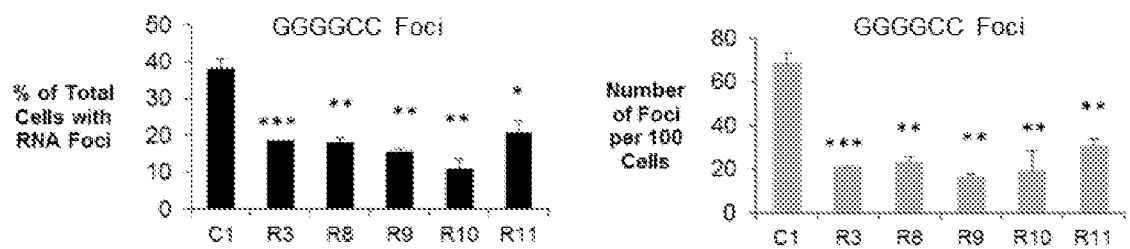
B.
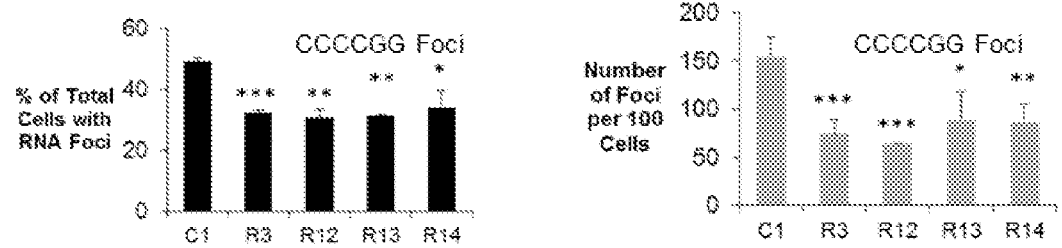
C.
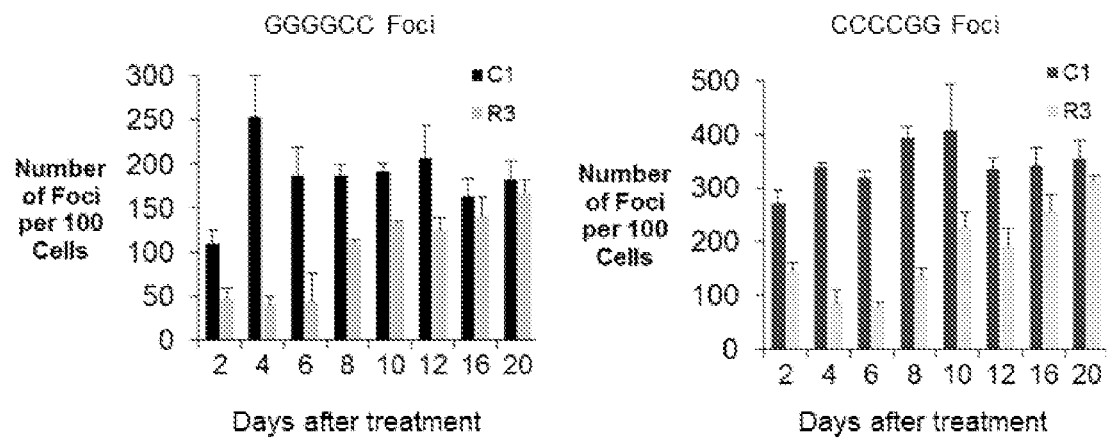
FIGS. 3A-C

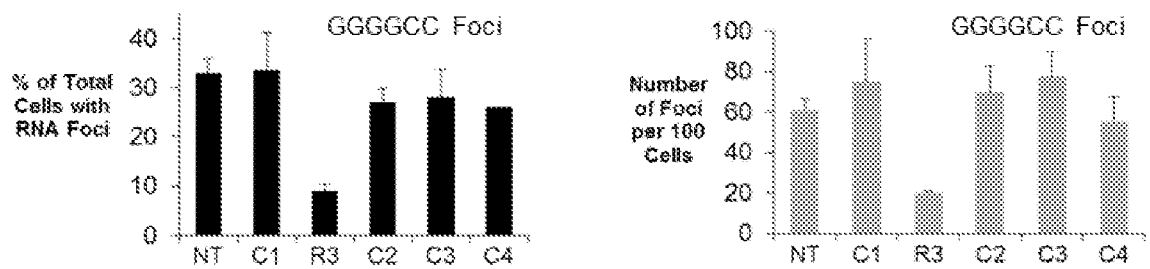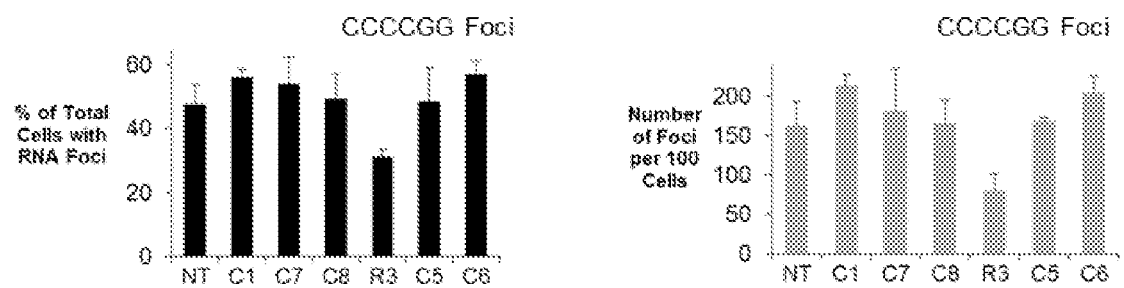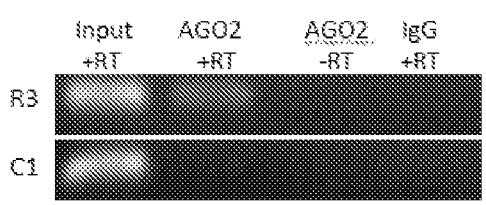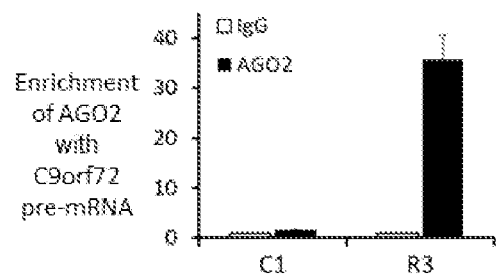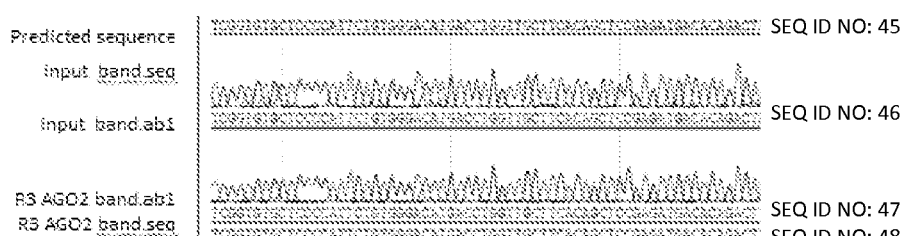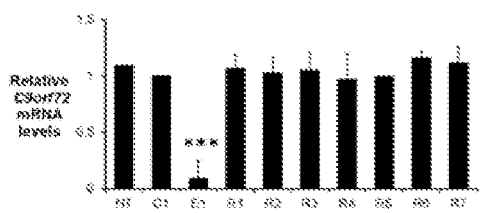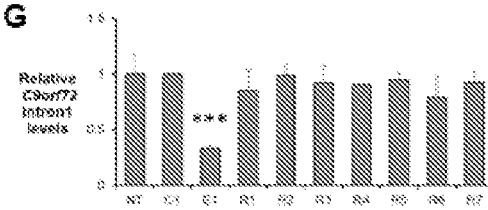
FIGS. 4A-G ALLELE SELECTIVE INHIBITION OF MUTANT C9ORF72 FOCI EXPRESSION BY DUPLEX RNAS TARGETING THE EXPANDED HEXANUCLEOTIDE REPEAT This application is a national phase application under 35 U.S.C. § 371 of International Application No. PCT/US2015/054594, filed Oct. 8, 2015, which claims benefit of priority to U.S. Provisional Application Ser. No. 62/063,548, filed Oct. 14, 2014, the entire contents of each of which are hereby incorporated by reference.

The invention was made with government support under Grant Nos. NIGMS 73042 and NIGMS 106151 awarded by the National Institutes of Health. The government has certain rights in the invention.

BACKGROUND

1. Field of the Disclosure

The present disclosure relates generally to the field of molecular biology, genetics and medicine. More particularly, it concerns compositions and methods for regulating the expression of GGGGCC-expansion disease genes, such as C9orf72, and thus the treatment of related diseases including amyotrophic lateral sclerosis (ALS) and frontotemporal dementia (FTD).

2. Description of Related Art

An expanded hexanucleotide repeat has been implicated in amyotrophic lateral sclerosis (ALS) and frontotemporal dementia (FTD). This repeat expansion occurs in the first intron of the chromosome 9 open reading frame 72 (C9orf72) gene. It accounts for one-third of familial ALS and a quarter of familial FTD (Renton et al., 2011; DeJesus-Hernandez et al., 2012). The sequence of the repeat within C9orf72 pre-mRNA is GGGGCC. Patients with ALS or FTD typically have one mutant C9orf72 allele that contains 700-1600 repeats, while unaffected individuals have fewer than 24 repeats in both alleles (DeJesus-Hernandez et al., 2012). The C9orf72 locus also expresses an antisense transcript that encodes a CCCCGG repeat that may contribute to disease (Gendron, 2013).

Expanded repeats may form structures that disrupt normal RNA-protein interactions, affect RNA processing, and contribute to pathogenesis (Ling et al., 2013). The expanded sense and antisense RNA transcripts are C/G rich and the G-rich sense strand is known to form a stable G-quadruplex structure (Haeusler et al., 2014). The expanded repeats and the structures they form may sequester proteins and disrupt normal function by decreasing the effective concentrations of associated proteins within cells (Lee et al., 2013). A similar mechanism of action has been demonstrated for the expanded CUG repeats that occur with the mutant DM protein kinase gene responsible for myotonic dystrophy (Wheeler et al., 2009). Because of their potential to disrupt normal processes in cells and contribute to disease, both the sense and antisense repeat transcripts at the C9orf72 locus are targets for inhibitors that block RNA, disrupt structure, and alter the potential for RNA-protein interactions.

Both ALS and FTD are currently incurable, leading to an urgent need for new insights into treatment. One strategy to blunt the impact of mutant C9orf72 RNA is to inhibit expression of the gene. Antisense oligonucleotides that are complementary to intronic regions within the C9orf72 transcript have been tested. These oligonucleotides were designed to recruit RNase H to their target sites and lead to degradation of intronic RNA. Introduction of these oligonucleotides into cells caused foci formation to decrease, and reduced RNA toxicity (Donnelly et al., 2013; Lagier-Tourenne et al., 2013; Sareen et al., 2013). However, there are a number of hurdles in applying this kind of technology to the treatment of diseases like ALS and FTD that remain to be overcome.

SUMMARY

Provided herein are a double-stranded oligonucleotides of 13 to 22 nucleobases in length targeting a GGGGCC expanded repeat region in an intron of C9orf72, comprises (a) 3-5 central mismatches (within bases 9-14) within a target sequence comprising the expanded repeat sequence, or (b) 3-5 mismatches outside of the seed sequence (bases 2-8 within the guide strand complementary to the expanded repeat sequence).

The oligonucleotide may comprise one or more chemically-modified nucleobases, such as a nuclease-resistant modification, including a modified sugar moiety or a modified internucleoside linkage. The modified sugar moiety may be a high-affinity sugar modification, such as a bicyclic sugar moiety, and in particular a 2'-modified sugar moiety, a 4' to 2' bicyclic sugar moiety, such as a 4'-CH$_2$—O-2' or 4'-CH(CH$_3$)—O-2' bicyclic sugar moiety, for example wherein each 4' to 2' bridge independently comprises from 2 to 4 linked groups independently selected from —[C(R$_a$)(R$_b$)]$_y$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_1$)—; wherein x is 0, 1, or 2; y is 1, 2, 3, or 4; each R$_a$ and R$_b$ is, independently, H, a protecting group, hydroxyl, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_5$-C$_9$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_5$-C$_{20}$ aryl, substituted C$_5$-C$_9$ aryl, acyl (C(=O)—H), substituted acyl, a heterocycle radical, a substituted heterocycle radical, C$_1$-C$_6$ aminoalkyl, substituted C$_1$-C$_6$ aminoalkyl or a protecting group. The double-stranded oligonucleotide of claim 10, wherein each 4' to 2' bridge is independently —[C(R$_c$)(R$_d$)]$_n$—, —[C(R$_c$)(R$_d$)]$_n$—O—, —C(R$_c$R$_d$)—N(R$_e$)—O— or —C(R$_e$R$_d$)—O—N(R$_e$)—, wherein each R$_c$ and R$_d$ is independently hydrogen, halogen, substituted or unsubstituted C$_1$-C$_6$ alkyl; and each R$_e$ is independently hydrogen or substituted or unsubstituted C$_1$-C$_6$ alkyl. In particular, each 4' to 2' bridge may be independently a 4'-(CH$_2$)$_2$-2',4'-(CH$_2$)$_3$-2',4'-CH$_2$—O-2',4'-CH(CH$_3$)—O-2',4'-(CH$_2$)$_2$—O-2',4'-CH$_2$—O—N(R$_e$)-2' and 4'-CH$_2$—N(R$_e$)—O-2'-bridge.

The double-stranded oligonucleotide may comprise terminal dT residues. The double-stranded oligonucleotide may comprise 3' and/or '5 2'-O-methyl modifications. The nucleobases may be linked by phosphate internucleoside linkages, such as wherein at least one of the phosphate internucleoside linkages is a phosphorothioate linkage, or wherein each internucleoside linkage is a phosphorothioate linkage. The double-stranded oligonucleotide comprises DNA nucleobases, RNA nucleobases or a mixture of DNA and RNA nucleobases. The central mismatches may comprise one or more abasic or unlocked nucleotides. Double-stranded oligonucleotide may be selected from the following RNAs, or a DNA cognate thereof:

| | | |
|---|---|---|
| CGGCCCCGAAACCGGCCCCdTdT | (AS) | SEQ ID NO: 1 |
| dTdTUCCGGGGCUUUGGCCGGGG | (S) | SEQ ID NO: 2 |
| CGGCCCCGAAAACGGCCCCdTdT | (AS) | SEQ ID NO: 3 |
| dTdTUCCGGGGCUUUUGCCGGGG | (S) | SEQ ID NO: 4 |
| CGGCCCCGAAAAACGGCCCCdTdT | (AS) | SEQ ID NO: 5 |
| dTdTUCCGGGGCUUUUGCCGGGG | (S) | SEQ ID NO: 6 |
| CGGCCCCGAAAACGACCCCdTdT | (AS) | SEQ ID NO: 7 |
| dTdTUCCGGGGCUUUUGCCGGGG | (S) | SEQ ID NO: 8 |
| CGGCCCCGAAAACGACCACdTdT | (AS) | SEQ ID NO: 9 |
| dTdTUCCGGGGCUUUUGCCGGGG | (S) | SEQ ID NO: 10 |
| CGGCCCCGAACCAGGACCCdTdT | (AS) | SEQ ID NO: 11 |
| dTdTUCCGGGGCUUGGUCCUGGG | (S) | SEQ ID NO: 12 |
| CGGCCCCGAACCAGACCCCdTdT | (AS) | SEQ ID NO: 13 |
| dTdTUCCGGGGCUUGGUCCUGGG | (S) | SEQ ID NO: 14 |
| CGGCCCCGAAACCGACCCCdTdT | (AS) | SEQ ID NO: 15 |
| dTdTUCCGGGGCUUUGGCCGGGG | (S) | SEQ ID NO: 16 |
| CGGCCCCGAACCCGACCCCdTdT | (AS) | SEQ ID NO: 17 |
| dTdTUCCGGGGCUUGGGCUGGG | (S) | SEQ ID NO: 18 |
| CGGCCCCGAAACCGACCCCdTdT | (AS) | SEQ ID NO: 19 |
| dTdTUCCGAGGCUUUGGCCGGGG | (S) | SEQ ID NO: 20 |
| CGGCCCCGAAACCGGCCCUdTdT | (AS) | SEQ ID NO: 21 |
| dTdTGCCGAGGCUUUGGCCGGGG | (S) | SEQ ID NO: 22 |
| CGGCCCCGAAACCGGCCCUdTdT | (AS) | SEQ ID NO: 23 |
| dTdTGCCGAGACCUUGGCCGGGG | (S) | SEQ ID NO: 24 |

Also provided is a method of selectively decreasing the expression of C9orf72 transcripts in a cell having an expanded GGGGCC repeat in an intron of C9orf72 comprising contacting the cell with a double-stranded oligonucleotide as described above. The expanded GGGGCC repeat region may contain 500 or more repeats, such as about 700 to 1600 repeats. The cell may be contacted with the double-stranded oligonucleotide at about 5-75 nM. The cell may be located in a subject suffering from a GGGGCC repeat disease, and contacting may comprise administering the double-stranded oligonucleotide by direct administration into the central nervous system, cerebrospinal fluid, or mediated uptake across the blood brain barriers. Contacting may also comprise administering the double-stranded oligonucleotide more than once. The method may further comprise administering a second therapeutic agent to the subject. The subject may have or exhibit a symptom of amyotrophic lateral sclerosis (ALS) and frontotemporal dementia (FTD). The method may result in reduced size or number of ALS/FTD foci in the brain tissue of the subject.

As used herein, the term "consisting essentially of" with regard to a nucleic acid sample means that the sample does not contain any material that does not fit the identified criteria, at least not at a readily detectable level. For example, a sample that consists essentially of RNA molecules less than 100 nt in length can mean that based on standard detection methods (e.g., gel electrophoresis or bioanalyzer analysis) the sample only contains negligible quantities of RNA molecules greater than 100 nt in length, preferably at such levels as cannot be detected by the standard detection methods. However, one of skill in the art will recognize that such a sample may contain longer RNA molecules, DNA molecules, proteins, or other cellular components, but only in such quantities as to not materially affect the basic characteristics of the sample. The term "consisting essentially of" is not meant to exclude the inclusion of buffers, salts, and other inert chemicals from being present in the sample.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, for the method being employed to determine the value, or that exists among the study subjects. Such an inherent variation may be a variation of ±10% of the stated value.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-B. Sense and antisense nuclear RNA foci are detected in C9orf72 patient derived fibroblast cells. (FIG. 1A) Scheme showing duplex RNAs targeting sense and antisense C9orf72 transcripts and the location of the expanded CCCCGG or GGGGCC repeat regions. (FIG. 1B) FISH images of expanded GGGGCC or CCCCGG RNA foci in wild-type control fibroblasts or C9orf72 patient derived fibroblasts. A $(CAG)_{10}$-Cy5 probe complementary to a CUG repeat was used as a control in C9orf72 fibroblasts.

FIGS. 2A-D. Inhibition of GGGGCC or CCCCGG foci by duplex RNAs evaluated by fluorescent microscopy. (FIG. 2A) Effect of duplex RNAs on detection of expanded GGGGCC repeat RNA with C9orf72 intronic RNA. (FIG. 2B) Sample microscopy images used for evaluating GGGGCC C9orf72 sense foci. (FIG. 2C) Effect of duplex RNAs on detection of expanded CCCCGG C9orf72 antisense transcript. (FIG. 2D) Sample microscopy images used for evaluating CCCCGG C9orf72 antisense foci. Error bars represent SEM. *$p<0.05$; $p<0.01$; *$p<0.001$ compared with control C1. At least one hundred cells were analyzed for each experiment.

FIGS. 3A-C. Optimizing inhibition of GGGGCC and CCCCGG foci. (FIG. 3A) Inhibition of GGGGCC foci by optimized duplex RNAs. (FIG. 3B) Inhibition of optimized CCCCGG foci by optimized duplex RNAs. (FIG. 3C) Time course showing effect of duplex RNA on foci number and foci per cell. Error bars represent SEM. *$p<0.05$; $p<0.01$; *$p<0.001$ compared with control C1. At least one hundred cells were analyzed for each experiment.

FIGS. 4A-G. Involvement of RNAi (FIG. 4A) Inhibition of GGGGCC foci is sequence-specific. (FIG. 4B) Inhibition of CCCCGG foci is sequence-specific. (FIG. 4C) RNA immunoprecipitation demonstrates recruitment of AGO2 to C9orf72 intronic RNA upon addition of duplex RNA. (FIG. 4D) Quantitation of enrichment of AGO2 on C9orf72 intronic RNA. (FIG. 4E) Sequencing of amplified product from RIP confirms identity as C9orf72 intronic RNA. At least one hundred cells were analyzed for each experiment in FIGS. 4A and 4B. (FIG. 4F) Quantitative PCR showing effect of duplex RNAs on levels of C9orf72 mRNA levels. (FIG. 4G) Quantitative PCR showing effect of duplex RNAs on levels of C9orf72 intron 1 RNA. Error bays represent SEM. ***p<0.001 relative to treatment with noncomplementary control RNA C1. NT: no treatment.

DESCRIPTION OF ILLUSTRATIVE EMBODIMENTS

The inventors hypothesized that duplex RNAs complementary to the expanded repeat would target the GGGGCC and CCCCGG repeats simultaneously. Previous work had shown that it was possible to use duplex RNAs to target expanded trinucleotide repeats. The inventors' laboratory and others had previously developed engineered duplex RNAs that target genes containing expanded CAG trinucleotide repeats (Hu et al., 2010; Fiszer et al., 2011).

The C9orf72 GGGGCC or CCCCGG repeats, however, pose novel challenges to recognition that go beyond past experience targeting CAG repeats. One challenge is that, unlike CAG repeats, the GGGGCC repeat is intronic rather than within an exon. The GGGGCC and CCCCGG foci are detected in cell nuclei, rather than cytoplasm. A second challenge, therefore, is that recognition by duplex RNA would need to occur in cell nuclei and involve nuclear RNAi rather than the more familiar cytoplasmic RNAi mechanism.

A third challenge is that RNA duplexes with high C/G content are considered to be poor candidates for gene silencing by RNAi (Petri and Meister, 2013). High C/G content impairs both strand loading and target recognition. RNA duplexes that are CG-rich will not readily unwind to release the RNA guide strand. Target RNA transcripts that are C/G rich are likely to form strong secondary structures that will resist binding by complementary small RNAs.

The inventors investigated whether duplex RNAs can also block foci formation and whether a single duplex RNA can interfere with foci formed by both the sense GGGGCC transcript and the antisense CCCCGG transcript. Duplex RNAs would have the advantage of using the potent RNAi mechanism and inhibiting both transcripts with one agent. The inventors report here that the previously noted challenges can be overcome, namely, that duplex RNAs can be engineered to overcome the barriers of high G/C content, function inside cell nuclei, recognize GGGGCC and CCCCGG repeats, and inhibit both sense and antisense strand foci. These and other aspects of the disclosure are set forth in detail below.

I. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21.sup.st edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2.sup.nd Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-F ANA" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings);

replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 2'-endo furanosyl nucleosides and RNA surrogates.

As used herein, "2'-endo-furanosyl nucleoside" means an RNA-like nucleoside that comprises a substituted sugar moiety that has a 2'-endo conformation. 2'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "phosphorous moiety" refers to a to monovalent P$^V$ phosphorus radical group. In certain embodiments, a phosphorus moiety is selected from: a phosphate, phosphonate, alkylphosphonate, aminoalkyl phosphonate, phosphorothioate, phosphoramidite, alkylphosphonothioate, phosphorodithioate, thiophosphoramidate, phosphotriester and the like.

The term "phosphate moiety" as used herein, refers to a terminal phosphate group that includes unmodified phosphates (—O—P(=O)(OH)OH) as well as modified phosphates. Modified phosphates include but are not limited to phosphates in which one or more of the O and OH groups is replaced with H, O, S, N(R) or alkyl where R is H, an amino protecting group or unsubstituted or substituted alkyl.

As used herein, "phosphate stabilizing modification" refers to a modification that results in stabilization of a 5'-phosphate moiety of the 5'-terminal nucleoside of an oligonucleotide, relative to the stability of an unmodified 5'-phosphate of an unmodified nucleoside under biologic conditions. Such stabilization of a 5'-phophate group includes but is not limited to resistance to removal by phosphatases. Phosphate stabilizing modifications include, but are not limited to, modification of one or more of the atoms that binds directly to the phosphorus atom, modification of one or more atoms that link the phosphorus to the 5'-carbon of the nucleoside, and modifications at one or more other positions of the nucleoside that result in stabilization of the phosphate. In certain embodiments, a phosphate stabilizing modification comprises a carbon linking the phosphorous atom to the 5'-carbon of the sugar. Phosphate moieties that are stabilized by one or more phosphate stabilizing modification are referred to herein as "stabilized phosphate moieties."

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "single-stranded" means an oligomeric compound that is not hybridized to its complement and which lacks sufficient self-complementarity to form a stable self-duplex.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity is a reduction of a gain-of-function of an expanded repeat-containing nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, the term "expanded repeat-containing RNA" means a mutant RNA molecule having a nucleobase sequence that includes a repeat region having a predetermined number of nucleobases repeats, wherein the presence or length of the repeat region affects the normal processing, function, or activity of the RNA or corresponding protein.

As used herein, the term "corresponding wild-type RNA" means the non-mutant version of the expanded repeat-containing RNA having normal function and activity. Typically, corresponding wild-type RNA molecules comprise a repeat region which is shorter than that of an expanded repeat-containing RNA.

As used herein, "selectivity" refers to the ability of an antisense compound to exert an antisense activity on a target nucleic acid to a greater extent than on a non-target nucleic acid.

As used herein, "mutant selective" refers to a compound that has a greater effect on a mutant nucleic acid than on the corresponding wild-type nucleic acid. In certain embodiments, the effect of a mutant selective compound on the mutant nucleic acid is 2, 3, 4, 5, 6, 7, 8, 9, 10, 15, 20, 25, 30, 35, 40, 50, 100 or more than 100 times greater than the effect of the mutant selective compound on the corresponding wild-type nucleic acid. In certain embodiments, such selectivity results from greater affinity of the mutant selective compound for the mutant nucleic acid than for the corresponding wild-type nucleic acid. In certain embodiments, selectivity results from a difference in the structure of the mutant compared to the wild-type nucleic acid. In certain embodiments, selectivity results from differences in processing or sub-cellular distribution of the mutant and wild-type nucleic acids. In certain embodiments, some selectivity may be attributable to the presence of additional target sites in a mutant nucleic acid compared to the wild-type nucleic acid. For example, in certain embodiments, a target mutant allele comprises an expanded repeat region comprising more repeats than the wild-type allele. Thus, the wild-type allele has fewer sites available for hybridization of an antisense compound targeting the repeat region. In certain embodiments, a mutant selective compound has selectivity greater than the selectivity predicted by the increased number of target sites. In certain embodiments, the ratio of inhibition of a mutant allele to a wild-type allele is equal to or greater than the ratio of the number of repeats in the mutant allele to the wild-type allele. In certain embodiments, the ratio of inhibition of a mutant allele to a wild-type allele is greater than the ratio of the number of repeats in the mutant allele to the wild-type allele.

As used herein, "gain-of-function activity" means a biological activity attributed to an expanded repeat-containing RNA. For example, an expanded repeat-containing RNA may gain the ability to sequester ribonuclear proteins and impair the normal action of RNA processing in the nucleus (see Cooper, T. (2009) Cell 136, 777-793; O'Rourke, J R (2009) J. Biol. Chem. 284 (12), 7419-7423).

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A)

is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between inventorsen an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "parenteral administration," means administration through injection or infusion. Parenteral administration includes, but is not limited to, subcutaneous administration, intravenous administration, or intramuscular administration.

As used herein, "systemic administration" means administration to an area other than the intended locus of activity. Examples or systemic administration are subcutaneous administration and intravenous administration, and intraperitoneal administration.

As used herein, "subcutaneous administration" means administration just below the skin.

As used herein, "intravenous administration" means administration into a vein.

As used herein, "cerebrospinal fluid" or "CSF" means the fluid filling the space around the brain and spinal cord.

As used herein, "administration into the cerebrospinal fluid" means any administration that delivers a substance directly into the CSF.

As used herein, "intracerebroventricular" or "ICV" mean administration into the ventricular system of the brain.

As used herein, "intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

The term "kit" as used herein refers to one or more suitably aliquoted compositions or reagents for use in the methods of the present disclosure. The components of the kits may be packaged either in aqueous or lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the present disclosure also will typically include a means for containing the reagent containers in close confinement for commercial sale. Such containers may include injection or blow molded plastic containers into which the desired vials are retained, for example.

II. GGGGCC Expansion Disease States

A. Amyotrophic Lateral Sclerosis

Amyotrophic lateral sclerosis (ALS), also known as Lou Gehrig's disease and Charcot disease, is a specific disorder that involves the death of neurons. In the United Kingdom the term motor neurone disease (MND) is commonly used, while others use that term for a group of five conditions of which ALS is the most common. ALS is characterized by stiff muscles, muscle twitching, and gradually worsening weakness due to muscle wasting. This results in difficulty speaking, swallowing, and eventually breathing.

The cause is not known in 90% to 95% of cases. About 5-10% of cases are inherited from a person's parents. About half of these genetic cases are due to one of two specific genes. It results in the death of the neurons that control voluntary muscles. The diagnosis is based on a person's signs and symptoms with testing done to rule out other potential causes.

There is no cure for ALS, but the medication riluzole may extend life expectancy by about two to three months. Non-invasive ventilation may result in both improved quality and length of life. The disease usually starts around the age of 60 and in inherited cases around the age of 50. The average survival from onset to death is three to four years. About 10% survive longer than 10 years. Most die from respiratory failure. In much of the world, rates of ALS are unknown. In Europe and the United States, the disease affects about 2 people per 100,000 per year.

The disorder causes muscle weakness and atrophy throughout the body due to the degeneration of the upper and lower motor neurons. Individuals affected by the disorder may ultimately lose the ability to initiate and control all voluntary movement, although bladder and bowel function and the muscles responsible for eye movement are usually spared until the final stages of the disorder.

Cognitive function is generally spared for most people, although some (about 5%) also develop frontotemporal dementia. A higher proportion of people (30-50%) also have more subtle cognitive changes which may go unnoticed, but are revealed by detailed neuropsychological testing. Infrequently, ALS coexists in individuals who also experience dementia, degenerative muscle disorder, and degenerative bone disorder as part of a syndrome called multisystem proteinopathy. Sensory nerves and the autonomic nervous system are generally unaffected, meaning the majority of people with ALS maintain hearing, sight, touch, smell, and taste.

Initial Symptoms.

The start of ALS may be so subtle that the symptoms are overlooked. The earliest symptoms of ALS are muscle weakness and/or muscle atrophy. Other presenting symptoms include trouble swallowing or breathing, cramping, or stiffness of affected muscles; muscle weakness affecting an arm or a leg; and/or slurred and nasal speech. The parts of the body affected by early symptoms of ALS depend on which motor neurons in the body are damaged first.

About 75% of people contracting the disorder first experience weakness or atrophy in an arm or leg and this is known as "limb-onset" ALS. Awkwardness when walking or running or even tripping over or stumbling may be experienced and often this is marked by walking with a "dropped foot" which drags gently on the ground. Or if arm-onset, difficulty with tasks requiring manual dexterity such as buttoning a shirt, writing, or turning a key in a lock may be experienced. Occasionally, the symptoms remain confined to one limb for a long period of time or for the duration of the illness; this is known as monomelic amyotrophy.

About 25% of cases begin as progressive bulbar palsy termed "bulbar-onset" ALS. Initial symptoms will mainly be of difficulty speaking clearly or swallowing. Speech may become slurred, nasal in character, or quieter. There may be difficulty in swallowing and loss of tongue mobility. A smaller proportion of people experience "respiratory-onset" ALS, where the intercostal muscles that support breathing are affected first. A small proportion of people may also present with what appears to be frontotemporal dementia, but later progresses to include more typical ALS symptoms.

Over time, people experience increasing difficulty moving, swallowing (dysphagia), and speaking or forming words (dysarthria). Symptoms of upper motor neuron involvement include tight and stiff muscles (spasticity) and exaggerated reflexes (hyperreflexia) including an overactive gag reflex. An abnormal reflex commonly called Babinski's sign also indicates upper motor neuron damage. Symptoms of lower motor neuron degeneration include muscle weakness and atrophy, muscle cramps, and fleeting twitches of muscles that can be seen under the skin (fasciculations) although twitching is not a diagnostic symptom and more of a side effect so twitching would either occur after or accompany weakness and atrophy. Around 15-45% of people experience pseudobulbar affect, a neurological disorder also known as "emotional lability", which consists of uncontrollable laughter, crying, or smiling, attributable to degeneration of bulbar upper motor neurons, resulting in exaggeration of motor expressions of emotion. For ALS to be diagnosed, symptoms of both upper and lower motor neuron damage that cannot be attributed to other causes must be present.

Progression.

Although the order and rate of symptoms varies from person to person, most people eventually are not able to walk or use their hands and arms. They also lose the ability to speak and swallow food, while most end up on a portable ventilator, called bilevel positive airway pressure. The rate of progression can be measured using an outcome measure called the "ALS Functional Rating Scale Revised (ALSFRS-R)", a 12-item instrument administered as a clinical interview or patient-reported questionnaire that produces a score between 48 (normal function) and 0 (severe disability). Though the degree of variability is high and a small percentage of people have a much slower disorder, on average, patients lose about 0.9 FRS points per month. A survey-based study amongst clinicians showed that they rated a 20% change in the slope of the ALSFRS-R as being clinically meaningful. Regardless of the part of the body first affected by the disorder, muscle weakness and atrophy spread to other parts of the body as the disorder progresses. In limb-onset ALS, symptoms usually spread from the affected limb to the opposite limb before affecting a new body region, whereas in bulbar-onset ALS, symptoms typically spread to the arms before the legs.

Disorder progression tends to be slower in patients who are younger than 40 at onset, are mildly obese, have disorder restricted primarily to one limb, and those with primarily upper motor neuron symptoms. Conversely, progression is faster and prognosis poorer in people with bulbar-onset disorder, respiratory-onset disorder, and frontotemporal dementia. The CX3CR1 allelic variants have also been shown to have an effect on the disorder's progression and life expectancy.

Late Stages.

Although respiratory support can ease problems with breathing and prolong survival, it does not affect the progression of ALS. Most people with ALS die from respiratory failure, usually within three to five years from the onset of symptoms. The median survival time from onset to death is around 39 months, and only 4% survive longer than 10 years.

Difficulty in chewing and swallowing makes eating very difficult and increases the risk of choking or of aspirating food into the lungs. In later stages of the disorder, aspiration pneumonia can develop, and maintaining a healthy weight can become a significant problem that may require the insertion of a feeding tube. As the diaphragm and intercostal muscles of the rib cage that support breathing weaken, measures of lung function such as vital capacity and inspiratory pressure diminish. In respiratory-onset ALS, this may occur before significant limb weakness is apparent. Most people with ALS die of respiratory failure or pneumonia.

In late stages, the oculomotor nerve that controls the movements of the eye can be affected as can the extraocular muscles (EOMs). The eye movements remain unaffected largely until the later stages due to differences in the extraocular muscles compared to the skeletal muscles that are initially and readily affected. In the disease's final stages, a person's condition may resemble locked-in syndrome.

Eye Movement.

People with ALS may have difficulty in generating voluntary fast movements of the eye. The speed of eye movement is slower in people with ALS. Problems in generating smooth pursuit and convergence movements have also been noted. Testing the vestibulo-ocular reflex should help in identifying these problems. The electrooculography (EOG) technique measures the resting potential of the retina. EOG findings in people with ALS show progressive changes that correlate with disorder progression, and provide a measurement for clinically evaluating the effects of disorder progression on oculomotor activity. Additionally, EOG may allow earlier detection of problems with the eyes.

The embryonic lineage of EOMs differs from that of somite-derived muscles. EOMs are unique because they continuously remodel through life and maintain a population of active satellite cells during aging. EOMs have significantly more myogenic precursor cells than limb skeletal muscles.

Genetics.

About 5-10% of cases are directly inherited from a person's parents. Overall, first-degree relatives of an individual with ALS have a 1% risk of developing ALS. A defect on chromosome 21, which codes for superoxide dismutase, is associated with about 20% of familial cases of ALS, or about 2% of ALS cases overall. This mutation is believed to be transmitted in an autosomal dominant manner, and has over a hundred different forms of mutation. The most common ALS-causing mutation is a mutant SOD1 gene, seen in North America; this is characterized by an exceptionally rapid progression from onset to death. The most common mutation found in Scandinavian countries, D90A-

SOD1, is more slowly progressive than typical ALS, and people with this form of the disorder survive for an average of 11 years.

In 2011, a genetic abnormality known as a hexanucleotide repeat was found in a region called C9orf72, which is associated with ALS combined with frontotemporal dementia ALS-FTD, and accounts for some 6% of cases of ALS among white Europeans. The gene is also found in people of Filipino descent.

The UBQLN2 gene encodes production of the protein ubiquilin 2 in the cell, which is a member of the ubiquilin family and controls the degradation of ubiquitinated proteins. Mutations in UBQLN2 interfere with protein degradation, leading to neurodegeneration and causing dominantly inherited, chromosome X-linked ALS and ALS/dementia.

Management of ALS attempts to relieve symptoms and extend life expectancy. This supportive care is best provided by multidisciplinary teams of health care professionals working with the person and their caregivers to keep them as mobile and comfortable as possible.

As mentioned above, Riluzole (Rilutek) has been found to modestly improve survival. It lengthens survival by several months, and may have a greater survival benefit for those with a bulbar onset. It also extends the time before a person needs ventilation support. People taking it must be monitored for liver damage (occurring in about 10% of people taking the drug). It is approved by Food and Drug Administration (US) and recommended by the National Institute for Clinical Excellence (UK). Riluzole does not reverse damage already done to motor neurons.

Other medications may be used to help reduce fatigue, ease muscle cramps, control spasticity, and reduce excess saliva and phlegm. Drugs also are available to help patients with pain, depression, sleep disturbances, dysphagia, and constipation. Baclofen and diazepam are often prescribed to control the spasticity caused by ALS, and trihexyphenidyl or amitriptyline may be prescribed when people with ALS begin having trouble swallowing their saliva.

When the muscles that assist in breathing weaken, use of ventilatory assistance (intermittent positive pressure ventilation, bilevel positive airway pressure (BiPAP), or biphasic cuirass ventilation (BCV) may be used to aid breathing. Such devices artificially inflate the person's lungs from various external sources that are applied directly to the face or body. When muscles are no longer able to maintain oxygen and carbon dioxide levels, these devices may be used full-time. BCV has the added advantage of being able to assist in clearing secretions by using high-frequency oscillations followed by several positive expiratory breaths. People may eventually consider forms of mechanical ventilation (respirators) in which a machine inflates and deflates the lungs. To be effective, this may require a tube that passes from the nose or mouth to the windpipe (trachea) and for long-term use, an operation such as a tracheotomy, in which a plastic breathing tube is inserted directly in the person's windpipe through an opening in the neck.

Persons and their families should consider several factors when deciding whether and when to use one of these options. Ventilation devices differ in their effect on the person's quality of life and in cost. Although ventilation support can ease problems with breathing and prolong survival, it does not affect the progression of ALS. Patients need to be fully informed about these considerations and the long-term effects of life without movement before they make decisions about ventilation support and have deep discussions on quality of life. Some persons under long-term tracheotomy intermittent positive pressure ventilation with deflated cuffs or cuffless tracheotomy tubes (leak ventilation) are able to speak, provided their bulbar muscles are strong enough, though in all cases speech will be lost as the disease progresses. This technique preserves speech in some persons with long-term mechanical ventilation. Other persons may be able to use a speaking valve such as a Passey-Muir speaking valve with the assistance and guidance of a speech-language pathologist.

External ventilation machines that use the ventilation mode of BiPAP are frequently used to support breathing, initially at night, and later during the daytime, as well. The use of BPAP (more often referred to as noninvasive ventilation, NIV) is only a temporary remedy, however, and long before BPAP stops being effective, persons should decide whether to have a tracheotomy and long-term mechanical ventilation. At this point, some persons choose palliative hospice care.

Physical therapy plays a large role in rehabilitation for individuals with ALS. Specifically, physical and occupational therapists can set goals and promote benefits for individuals with ALS by delaying loss of strength, maintaining endurance, limiting pain, preventing complications, and promoting functional independence.

Occupational therapy and special equipment such as assistive technology can also enhance patients' independence and safety throughout the course of ALS. Gentle, low-impact aerobic exercise such as performing activities of daily living, walking, swimming, and stationary bicycling can strengthen unaffected muscles, improve cardiovascular health, and help patients fight fatigue and depression. Range of motion and stretching exercises can help prevent painful spasticity and shortening (contracture) of muscles. Physical and occupational therapists can recommend exercises that provide these benefits without overworking muscles. They can suggest devices such as ramps, braces, walkers, bathroom equipment (shower chairs, toilet risers, etc.), and wheelchairs that help patients remain mobile. Occupational therapists can provide or recommend equipment and adaptations to enable people to retain as much safety and independence in activities of daily living as possible.

ALS patients who have difficulty speaking may benefit from working with a speech-language pathologist. These health professionals can teach patients adaptive strategies such as techniques to help them speak louder and more clearly. As ALS progresses, speech-language pathologists can recommend the use of augmentative and alternative communication such as voice amplifiers, speech-generating devices (or voice output communication devices) and/or low tech communication techniques such as alphabet boards or yes/no signals.

B. Frontotemporal Dementia

Frontotemporal dementia (FTD), formerly known as disinhibition-dementia-parkinsonism-amyotrophy complex (DDPAC), is a neurodegenerative disease characterized by severe frontotemporal lobar degeneration. The disorder was first identified in 1994 by Kirk Wilhelmsen and colleagues, who distinguished it from Alzheimer's disease and Lewy body dementia based on the fact that it did not manifest with amyloid plaques, neurofibrillary tangles, or Lewy bodies. Second only to Alzheimer's disease (AD) in prevalence, FTD accounts for 20% of pre-senile dementia cases. Symptoms can begin to appear on average around 45 to 65 years of age, regardless of gender. The most common symptoms include significant changes in social and personal behavior, as well as a general blunting of emotions. Symptoms progress at a rapid, steady rate. Patients suffering from the disease can survive between 2-10 years. Eventually patients will need 24-hour care for daily function. Because FTD often occurs in younger people (i.e., in their 40's or 50's), it can severely affect families. Patients often still have children living in the home. Financially, it can be devastating as the disease strikes at the time of life that is often the top wage-earning years. Currently, there is no cure for FTD. Treatments are available to manage the behavioral symptoms. Disinhibition and compulsive behaviors can be controlled by selective serotonin reuptake inhibitors (SSRIs). Although Alzheimer's and FTD share certain symptoms, they cannot be treated with the same pharmacological agents because the cholinergic systems are not affected in FTD.

FTD is traditionally difficult to diagnose due to the heterogeneity of the associated symptoms. Symptoms are classified into three groups based on the functions of the frontal and temporal lobes. Behavioral variant FTD (bvFTD) exhibits symptoms of lethargy and aspontaneity on the one hand, and disinhibition on the other. Apathetic patients may become socially withdrawn and stay in bed all day or no longer take care of themselves. Disinhibited patients can make inappropriate (sometimes sexual) comments or perform inappropriate acts. Patients with FTD can sometimes get into trouble with the law because of inappropriate behavior such as stealing or speeding. Recent findings indicate that psychotic symptoms are rare in FTD, possibly due to limited temporal-limbic involvement. Among FTD patients, approximately 2% have delusions, sometimes with paranoid ideation. Hallucinations are rare. These psychotic symptoms are significantly less prevalent than what is seen in AD patients, where approximately 20% have delusions and paranoia. Progressive nonfluent aphasia (PNFA) presents with a breakdown in speech fluency due to articulation difficulty, phonological and/or syntactic errors but preservation of word comprehension. Semantic dementia (SD) can be found in some patients that remain fluent with normal phonology and syntax, but increasing difficulty with naming and word comprehension. It has been researched that some may even go through depression and lose their inhibitions and exhibit antisocial behavior.

FTD patients tend to struggle with binge eating and compulsive behaviors. These binge eating habits are often associated with abnormal eating behavior including overeating, stuffing oneself with food, changes in food preferences (cravings for more sweets, carbohydrates), eating inedible objects and snatching food from others. Recent findings have indicated that the neural structures responsible for eating changes in FTD include atrophy in the right ventral insula, striatum and orbitofrontal cortex on structural MRI voxel-based morphometry (right hemisphere).

Executive function is the cognitive skill of planning and organizing. Most FTD patients become unable to perform skills that require complex planning or sequencing. In addition to the characteristic cognitive dysfunction, a number of primitive reflexes known as frontal release signs are often able to be elicited. Usually, the first of these frontal release signs to appear is the palmomental reflex which appears relatively early in the disease course whereas the palmar grasp reflex and rooting reflex appear late in the disease course. The following abilities in the FTD patients are preserved: perception, spatial skills, memory, praxis, The following abilities in FTD patients are affected: social behavior/conduct, regulation of emotion, ability to focus, utilization behavior (neurobehavioral disorder where the patients grab objects in view and start to conduct the right behavior at the wrong time), and inappropriate speech/actions.

In rare cases, FTD can occur in patients with motor neuron disease (MND) (typically amyotrophic lateral sclerosis). The prognosis for people with MND is worse when combined with FTD, shortening survival by about a year. A number of case series have now been published looking at the pathological basis of frontotemporal dementia. As with other syndromes associated with frontotemporal lobar degeneration (FTLD), a number of different pathologies are associated with FTD:

Tau pathology: In a healthy individual, tau proteins stabilize microtubules, which are major component of the cytoskeleton. Examples include Pick's disease, now also referred to as FTLD-tau, and other tau-positive pathology including FTDP-17, corticobasal degeneration, and progressive supranuclear palsy. Approximately 50% of FTD cases will present with tau pathology at post-mortem.

TDP-43 pathology: This disease form was previously described as dementia with ubiquitin positive, tau- and alpha-synuclein negative inclusions with and without motor neuron degeneration. FTLD-TDP43 accounts for approximately 40% of FTD (±MND).

FUS pathology: Cases with underlying FUS pathology tend to present with behavioral variant FTD (bvFTD), but the correlation is by no means reliable enough to predict the post-mortem pathology. FTLD-FUS represents only 5-10% of clinically diagnosed FTD.

Dementia lacking distinctive histology (DLDH) is a rare entity and represents the remaining small percentage of FTD that cannot be positively diagnosed as any of the above at post-mortem.

In rare cases, patients with clinical FTD were found to have changes consistent with Alzheimer's disease on autopsy Evidence suggests that FTD selectively impairs spindle neurons, a type of neuron which has only been found in the brains of humans, great apes, and whales. Deficiencies of the micronutrients folate and B12 have been associated with cognitive impairment in individuals with FTD. Chronic folate deficiency has also been implicated in cerebral atrophy, leading to neurological impairment.

Structural MRI scans often reveal frontal lobe and/or anterior temporal lobe atrophy but in early cases the scan may seem normal. Atrophy can be either bilateral or asymmetric. Registration of images at different time points of time (e.g., one year apart) can show evidence of atrophy that otherwise (at individual time points) may be reported as normal. Many research groups have begun using techniques such as magnetic resonance spectroscopy, functional imaging and cortical thickness measurements in an attempt to offer an earlier diagnosis to the FTD patient. Fluorine-18-Fluorodeoxyglucose Positron Emission Tomography (FDG-PET) scans classically show frontal and/or anterior temporal hypometabolism, which helps differentiate the disease from Alzheimer's disease. The PET scan in Alzheimer's disease classically shows biparietal hypometabolism. Meta-analyses based on imaging methods have shown that frontotemporal dementia mainly affects a frontomedial network discussed in the context of social cognition or 'theory of mind'. This is entirely in keeping with the notion that on the basis of cognitive neuropsychological evidence, the ventromedial prefrontal cortex is a major locus of dysfunction early on in the course of the behavioural variant of frontotemporal degeneration. The language subtypes of frontotemporal lobar degeneration (semantic dementia and progressive nonfluent aphasia) can be regionally dissociated by imaging approaches in vivo.

The confusion between Alzheimer's and FTD is justifiable due to the similarities between their initial symptoms.

Patients do not have difficulty with movement and other motor tasks. As FTD symptoms appear, it is difficult to differentiate between a diagnosis of Alzheimer's disease and FTD. There are distinct differences in the behavioral and emotional symptoms of the two dementias, notably, the blunting of emotions seen in FTD patients. In the early stages of FTD, anxiety and depression are common, which may result in an ambiguous diagnosis. However, over time, these ambiguities fade away as this dementia progresses and defining symptoms of apathy, unique to FTD, start to appear.

In vivo brain imaging of tau aggregation in frontotemporal dementia using [F-18]FDDNP positron emission tomography is more visual and has enhanced the ability to have a deeper understanding in frontal temporal dementia. Previous fluorescent microscopy studies of Alzheimer's disease (AD) brain specimens have shown that [F-18] FDDNP displays an excellent visualization of interneuronal neurofibrillary tangles (NFTs). Visual images of [F-18]FDDNP-PET images emphasized a frontal signal in FTD compared to prominent temporal signals in AD. [F-18]FDDNP-PET has allowed the enhanced visualization of tauopathies in patients. This has aided in differentiating FTD from parietal and temporal signals in AD. Further, the ability of [F-18] FDDNP to entitle tauopathies in vivo gives a tool for monitoring the effect of therapies to eliminate NFT accumulation. Recent studies over several years have developed new criteria for the diagnosis of behavioral variant frontotemporal dementia (bvFTD). Six distinct clinical features have been identified as symptoms of bvFTD:

Disinhibition
Apathy/Inertia
Loss of Sympathy/Empathy
Perseverative/compulsive behaviors
Hyperorality
Dysexecutive neuropsychological profile Of the six features, three must be present in a patient to diagnose one with possible bvFTD. Similar to standard FTD, the primary diagnosis stems from clinical trials that identify the associated symptoms, instead of imaging studies. The above criteria are used to distinguish bvFTD from disorders such as Alzheimer's and other causes of dementia. In addition, the new criteria allow for a diagnostic hierarchy distinguished possible, probable, and definite bvFTD based on the number of symptoms present.

A higher proportion of FTD cases seem to have a familial component than more common neurodegenerative diseases like Alzheimer's disease. More and more mutations and genetic variants are being identified all the time, so the lists of genetic influences require consistent updating. Tau-positive frontotemporal dementia with parkinsonism (FTDP-17) is caused by mutations in the MAPT gene on chromosome 17 that encodes the Tau protein It has been determined that there is a direct relationship between the type of tau mutation and the neuropathology of gene mutations. The mutations at the splice junction of exon 10 of tau lead to the selective deposition of the repetitive tau in neurons and glia. The pathological phenotype associated with mutations elsewhere in tau is less predictable with both typical neurofibrillary tangles (consisting of both 3 repeat and 4 repeat tau) and Pick bodies (consisting of 3 repeat tau) having been described). The presence of tau deposits within glia is also variable in families with mutations outside of exon 10. This disease is now informally designated FTDP-17T. FTD shows a linkage to the region of the tau locus on chromosome 17, but it is believed that there are two loci leading to FTD within megabases of each other on chromosome 17. FTD caused by FTLD-TDP43 has numerous genetic causes.

Some cases are due to mutations in the GRN gene, also located on chromosome 17. Others are caused by VCP mutations, although these patients present with a complex mixture of Inclusion body myopathy, Paget's disease of bone, and FTD. The most recent addition to the list is a hexanucleotide repeat expansion in the promotor region of C9ORF72. Only one or two cases have been reported describing TARDBP (the TDP-43 gene) mutations in a clinically pure FTD (FTD without MND).

III. Oligonucleotide Agents

The oligonucleotide agents of the present disclosure are double-stranded oligonucleotides of 13 to 22 nucleobases in length and having a repeating tri-nucleobase sequence comprising (i) GGGGCC or (ii) GGCCCC. The length of the oligonucleotide may be 13, 14, 15, 16, 17, 18, 19, 20, 21 or 22 nucleobases. The oligonucleotides may, in particular, be RNA and include one or more modified and/or non-natural nucleobases. The oligonucleotide may contain DNA as well as RNA nucleobases, such as terminal thymidine residues. In particular, the oligonucleotides may be represented by the specific sequences:

| | | |
|---|---|---|
| CGGCCCCGAAACCGGCCCCdTdT | (AS) | SEQ ID NO: 1 |
| dTdTUCCGGGGCUUUGGCCGGGG | (S) | SEQ ID NO: 2 |
| CGGCCCCGAAAACGGCCCCdTdT | (AS) | SEQ ID NO: 3 |
| dTdTUCCGGGGCUUUUGCCGGGG | (S) | SEQ ID NO: 4 |
| CGGCCCCAAAAACGGCCCCdTdT | (AS) | SEQ ID NO: 5 |
| dTdTUCCGGGGCUUUUGCCGGGG | (S) | SEQ ID NO: 6 |
| CGGCCCCGAAAACGACCCCdTdT | (AS) | SEQ ID NO: 7 |
| dTdTUCCGGGGCUUUUGCCGGGG | (S) | SEQ ID NO: 8 |
| CGGCCCCGAAAACGACCACdTdT | (AS) | SEQ ID NO: 9 |
| dTdTUCCGGGGCUUUUGCCGGGG | (S) | SEQ ID NO: 10 |
| CGGCCCCGAACCAGGACCCCdTdT | (AS) | SEQ ID NO: 11 |
| dTdTUCCGGGGCUUGGUCCUGGGG | (S) | SEQ ID NO: 12 |
| CGGCCCCGAACCAGACCCCdTdT | (AS) | SEQ ID NO: 13 |
| dTdTUCCGGGGCUUGGUCCUGGGG | (S) | SEQ ID NO: 14 |
| CGGCCCCGAAACCGACCCCdTdT | (AS) | SEQ ID NO: 15 |
| dTdTUCCGGGGCUUUGGCCGGGG | (S) | SEQ ID NO: 16 |
| CGGCCCCGAACCCGACCCCdTdT | (AS) | SEQ ID NO: 17 |
| dTdTUCCGGGGCUUGGGCUGGGG | (S) | SEQ ID NO: 18 |
| CGGCCCCGAAACCGACCCCdTdT | (AS) | SEQ ID NO: 19 |
| dTdTUCCGAGGCUUUGGCCGGGG | (S) | SEQ ID NO: 20 |
| CGGCCCCGAAACCGGCCCUdTdT | (AS) | SEQ ID NO: 21 |
| dTdTGCCGAGGCUUUGGCCGGGG | (S) | SEQ ID NO: 22 |
| CGGCCCCGAAACCGGCCCUdTdT | (AS) | SEQ ID NO: 23 |
| dTdTGCCGAGACCUUGGCCGGGG | (S) | SEQ ID NO: 24 |

Another design consideration is the placement of 3, 4 or 5 "mismatches" in the double-stranded RNA as compared to the target sequence. In one embodiment, the mismatches are generally "centrally located" in the RNA, i.e., not located within the first two or last two bases of the RNA. A more restrictive definition of centrally located would be the center 3-4 bases, or in the center base (for an odd number of bases) or one or both of the center bases (for an even number of bases). More particularly, on a nucleic acid of at least 15 residues in length, there should be at least 7 residues flanking each side of the mismatch base, or on a nucleic acid of at least 16 residues in length, there should be at least 7 residues flanking two adjacent mismatched bases. Though any mismatch is useful, of particular interest are purine mismatches, such as introducing an adenosine base into the guide strand.

Another type of "mismatch" is an abasic nucleotide, i.e., one that lacks the base component. The are also called AP sites (apurinic/apyrimidinic site), and are found naturally in DNA, and also in RNA but less often. As the name suggests, the based has neither a purine nor a pyrimidine base, either spontaneously or due to DNA damage. It has been estimated that under physiological conditions 10,000 apurinic sites and 500 apyrimidinic may be generated in a cell daily.

In nature, AP sites can be formed by spontaneous depurination, but also occur as intermediates in base excision repair. In this process, a DNA glycosylase recognizes a damaged base and cleaves the N-glycosidic bond to release the base, leaving an AP site. A variety of glycosylases that recognize different types of damage exist, including oxidized or methylated bases, or uracil in RNA. The AP site can then be cleaved by an AP endonuclease, leaving 3' hydroxyl and 5' deoxyribosephosphate termini (see DNA structure). In alternative fashion, bifunctional glycosylase-lyases can cleave the AP site, leaving a 5' phosphate adjacent to a 3' α,β-unsaturated aldehyde. Both mechanisms form a single-strand break, which is then repaired by either short-patch or long-patch base excision repair.

Yet another "mismatch" is an unlocked nucleic acid (UNA). These 2',3'-seco-RNA chemical modifications thermodynamically destabilizes RNA duplexes, yet preserve the A-form helix of double stranded RNA, and also have the advantageous property of reduced seed-based off-target effects and, when placed at the 2 nucleotide (nt) 3' overhang position, can confer increased nuclease stability. Furthermore, placement of a UNA at the first (i.e., 5' terminal) or second position of one strand of an siRNA impairs the gene-silencing ability of the modified strand. This termed "strand-blocking."

Another consideration is to avoid multiple changes in the "seed" sequence of the double-stranded RNA, i.e., the first 8 bases. Thus, in a double-stranded RNA of at least 19 bases, there would no or one mismatches in 2-8 bases, and 3-5 mismatches in bases 9-14, or in bases 15 to the 3'-terminus. In other words, with respect to multiple mismatches, these can be either in the guide strand, or in both strands, and only one mismatch should occur in the seed region. In addition, to mismatches, it is contemplated that the guide strand may contain a base insertion with respect to the passenger strand.

In addition to double-stranded RNAs, ss-siRNAs are a new approach to gene silencing in which single-stranded RNA is chemically modified to enable it to be stable in vivo while retaining the ability to engage the RNAi machinery (Lima et al., 2012). The inventors have previously shown that anti-CAG ss-siRNAs can be active towards inhibiting expression of CAG repeat containing genes in cell culture and the central nervous system of HD model mice. ss-siRNAs are attractive candidates for testing because, in contrast to duplex RNA, they are single-stranded and may possess better biodistribution and activity in vivo. Thus, the inventors contemplate the application of ss-siRNAs as GGGGCC/CCCCGG repeat targeting agents.

Single-stranded antisense oligonucleotides (ASOs) should also bind directly to the GGGGCC/CCCCGG repeat. ASOs will not require the RNAi machinery and are a different strategy for silencing gene expression. The inventors contemplate ASOs substituted with locked nucleic acids (LNAs). LNA nucleotides are constrained by a bond between the 2' and 4' positions of the ribose ring. This constraint "locks" the nucleotide into a position that is ideal for base-pairing and the introduction of a handful of LNA nucleotides into an ASO can tailor the affinity of an ASO for optimal success in many applications. Thus, the inventors also contemplate the application of ASOs as GGGGCC/CCCCGG repeat targeting agents.

Commercially available equipment routinely used for the support media based synthesis of oligomeric compounds and related compounds is sold by several vendors including, for example, Applied Biosystems (Foster City, Calif.), General Electric, as well as others. Suitable solid phase techniques, including automated synthesis techniques, are described in Scozzari and Capaldi, "Oligonucleotide Manufacturing and Analysic Processes for 2'-O-(2-methoxyethyl-Modified Oligonucleotides" in Crooke, S. T. (ed.) ANTISENSE THERAPEUTICS (2008).

IV. Modified Nucleobases

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH═CH$_2$, O—CH$_2$—CH═CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(═O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O(CH$_2$)$_2$—O—N(CH$_3$)$_2$, —O(CH$_2$)$_2$O(CH$_2$)$_2$N(CH$_3$)$_2$, and O—CH$_2$—C(═O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$. Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2',4'-(CH$_2$)$_2$-2',4'-(CH$_2$)—O-2' (LNA), 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya et al., J. Org. Chem., 2009, 74, 118-134); and 4'-CH$_2$—C(═CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)═C(R$_b$)—, —C(R$_a$)═N—, —C(═NR$_a$)—, —C(═O)—, —C(═S)—, —O—, —Si(R$_a$)$_2$—, —S(═O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(═O)—H), substituted acyl, CN, sulfonyl (S(═O)$_2$-J$_1$), or sulfoxyl (S(═O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(═O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH2-O-2') BNA, (B) β-D-Methyleneoxy (4'-CH2-O-2') BNA (also referred to as locked nucleic acid or LNA), (C) Ethyleneoxy (4'-(CH2)2-O-2') BNA, (D) Aminooxy (4'-CH2-O—N(R)-2') BNA, (E) Oxyamino (4'-CH2-N(R)—O-2') BNA, (F) Methyl(methyleneoxy) (4'-CH(CH3)-O-2') BNA (also referred to as constrained ethyl or cEt), (G) methylene-thio (4'-CH2-S-2') BNA, (H) methylene-amino (4'-CH2-N(R)-2') BNA, (I) methyl carbocyclic (4'-CH2-CH(CH3)-2') BNA, (J) propylene carbocyclic (4'-(CH2)3-2') BNA, and (K) Methoxy(ethyleneoxy) (4'-CH(CH2OMe)-O-2') BNA (also referred to as constrained MOE or cMOE).

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the .alpha.-L configuration or in the β-D configuration. Previously, α-L-methyleneoxy (4'-CH2-O-2') bicyclic nucleosides have been incorporated into antisense oligonucleotides that showed antisense activity (Frieden et al., Nucleic Acids Research, 2003, 21, 6365-6372).

In certain embodiments, substituted sugar moieties comprise one or more non-bridging sugar substituent and one or more bridging sugar substituent (e.g., 5'-substituted and 4'-2' bridged sugars; PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US20050130923, published on Jun. 16, 2005) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), and fluoro HNA (F-HNA).

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854).

Combinations of modifications are also provided without limitation, such as 2'-F-5'-methyl substituted nucleosides (see PCT International Application WO2008/101157 Published on Aug. 21, 2008 for other disclosed 5',2'-bis substituted nucleosides) and replacement of the ribosyl ring oxygen atom with S and further substitution at the 2'-position (see U.S. Patent Publication US20050130923, published on Jun. 16, 2005) or alternatively 5'-substitution of a bicyclic nucleic acid (see PCT International Application WO2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In certain embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine ($^2$H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., Angewandte Chemie, International Edition, 1991, 30, 613; and those disclosed by Sanghvi, Y. S., Chapter 15, Antisense Research and Applications, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, each of which is herein incorporated by reference in its entirety.

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, phosphoramidate, and phosphorothioates (P═S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C (O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-

CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-5-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylamino-carbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

V. Pharmaceutical Formulations

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423. Compositions of the present disclosure comprise an effective amount of the oligonucleotide to cells, dissolved or dispersed in a pharmaceutically acceptable carrier or medium.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, liposomes, cationic lipid formulations, microbubble nanoparticles, and the like. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. This includes oral, nasal, buccal, or topical. Alternatively, administration may be by intradermal, subcutaneous, intramuscular, intraperitoneal or intravenous injection, or introduction into the CNS, such as into spinal fluid. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the oligonucleotides of the present disclosure may be incorporated with excipients. The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Of particular interest to the present disclosure is the use of lipid delivery vehicles. Lipid vehicles encompass micelles, microemulsions, macroemulsions, liposomes, and similar carriers. The term micelles refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10 100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 μm.

In one embodiment of a liposome formulation, the principal lipid of the vehicle may be phosphatidylcholine. Other useful lipids include various natural (e.g., tissue derived L-α-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a secondary lipid. Such secondary helper lipids may be non-ionic or uncharged at physiological pH, including non-ionic lipids such as cholesterol and DOPE (1,2-dioleolylglyceryl phosphatidylethanolamine). The molar ratio of a phospholipid to helper lipid can range from about 3:1 to about 1:1, from about 1.5:1 to about 1:1, and about 1:1.

Another specific lipid formulation comprises the SNALP formulation, containing the lipids 3-N-[(ω methoxypoly (ethylene glycol)$_{2000}$) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar % ratio.

Exemplary amounts of lipid constituents used for the production of the liposome include, for instance, 0.3 to 1 mol, 0.4 to 0.6 mol of cholesterol; 0.01 to 0.2 mol, 0.02 to 0.1 mol of phosphatidylethanolamine; 0.0 to 0.4 mol, or 0-0.15 mol of phosphatidic acid per 1 mol of phosphatidylcholine.

Liposomes can be constructed by well-known techniques. Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase, but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, 1978). Unilamellar vesicles can also be prepared by sonication or extrusion. Sonication is generally performed with a bath-type sonifier, such as a Branson tip sonifier (G. Heinemann Ultrashall and Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes can also be formed by extrusion through an asymmetric ceramic filter, such as a Ceraflow Microfilter (commercially available from the Norton Company, Worcester, Mass.).

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present disclosure, liposomes have a size of about 0.05 microns to about 0.5 microns, or having a size of about 0.05 to about 0.2 microns.

VI. Methods of Delivering Oligonucleotides

In certain embodiments, the oligonucleotide compounds and compositions as described herein are administered parenterally. In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, oligonucleotide compounds and compositions are delivered to the CNS. In certain embodiments, oligonucleotide compounds and compositions are delivered to the cerebrospinal fluid. In certain embodiments, oligonucleotide compounds and compositions are administered to the brain parenchyma. In certain embodiments, oligonucleotide compounds and compositions are delivered to an animal by intrathecal administration, or intracerebroventricular administration. Broad distribution of oligonucleotide compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

In certain embodiments, delivery of an oligonucleotide compound or composition described herein can affect the pharmacokinetic profile of the oligonucleotide compound or composition. In certain embodiments, injection of a oligonucleotide compound or composition described herein, to a targeted tissue improves the pharmacokinetic profile of the oligonucleotide compound or composition as compared to infusion of the oligonucleotide compound or composition. In a certain embodiment, the injection of an oligonucleotide compound or composition improves potency compared to broad diffusion, requiring less of the compound or composition to achieve similar pharmacology. In certain embodiments, similar pharmacology refers to the amount of time that a target mRNA and/or target protein is down-regulated (e.g., duration of action). In certain embodiments, methods of specifically localizing a pharmaceutical agent, such as by bolus injection, decreases median effective concentration ($EC_{50}$) by a factor of about 50 (e.g., 50-fold less concentration in tissue is required to achieve the same or similar pharmacodynamic effect). In certain embodiments, methods of specifically localizing a pharmaceutical agent, such as by bolus injection, decreases median effective concentration ($EC_{50}$) by a factor of 20, 25, 30, 35, 40, 45 or 50.]

In certain embodiments, delivery of an oligonucleotide compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days. In certain embodiments, delivery to the CNS is by intraparenchymal administration, intrathecal administration, or intracerebroventricular administration.

In certain embodiments, an oligonucleotide is delivered by injection or infusion once every week, every two weeks, every month, every two months, every 90 days, every 3 months, every 6 months, twice a year or once a year.

VII. Combination Therapies

It is common in many fields of medicine to treat a disease with multiple therapeutic modalities, often called "combination therapies." In the present application, the inventors contemplate using combination therapies to treat ALS or FTD. Such combinations will include the oligonucleotides according to the present disclosure, along with one or more "standard" therapeutic modalities.

Thus, to treat ALS or FTD, one would generally contact a target cell or subject with an oligonucleotide and at least one other therapy. These therapies would be provided in a combined amount effective to achieve a reduction in one or more disease parameter. This process may involve contacting the subjects with the both agents/therapies at the same time, e.g., using a single composition or pharmacological formulation that includes both agents, or by contacting the cell/subject with two distinct compositions or formulations, at the same time, wherein one composition includes the oligonucleotide and the other includes the other agent.

Alternatively, the oligonucleotide may precede or follow the other treatment by intervals ranging from minutes to weeks. One would generally ensure that a significant period of time did not expire between each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the oligonucleotide or the other therapy will be desired. Various combinations may be employed, where the oligonucleotide is "A," and the other therapy is "B," as exemplified below:

A/B/A B/A/B B/B/A A/A/B B/A/A A/B/B B/B/B/A B/B/
A/B A/A/B/B A/B/A/B A/B/B/A B/B/A/A B/A/B/A
B/A/A/B B/B/B/A A/A/A/B B/A/A/A A/B/A/A A/A/
B/A A/B/B/B B/A/B/B B/B/A/B

Other combinations are contemplated. As discussed above, other therapies have been used to treat ALS and FTD and can be used in combination with the oligonucleotide therapies described herein.

VIII. Kits

Any of the compositions described herein may be comprised in a kit. In a non-limiting example, an oligonucleotide targeting a tri-nucleobase repeat is included in a kit. The kit may further include a sterile buffer to facilitate dilution. The kit may also include one or more devices for delivery, such as a syringe, catheter, inhaler or aerosol delivery device.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present disclosure also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

The kits of the present disclosure will also typically include a means for containing the vials in close confinement for commercial sale, such as, e.g., injection and/or blow-molded plastic containers into which the desired vials are retained. A kit will also include instructions for employing the kit components as well the use of any other reagent not included in the kit. Instructions may include variations that can be implemented.

It is contemplated that such reagents are embodiments of kits of the disclosure. Such kits, however, are not limited to the particular items identified above and may include any reagent used for the manipulation or delivery of oligonucleotides.

IX. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Cell Culture and siRNA Transfection.

C9orf72 patient-derived fibroblast cell line is a gift from Dr. John Ravits of UCSD. The fibroblasts were maintained at 37° C. and 5% $CO_2$ in Minimal Essential Media Eagle (MEM) (Sigma, M4655) supplemented with 15% heat inactivated fetal bovine serum (Sigma) and 0.5% MEM nonessential amino acids (Sigma).

siRNAs were obtained from IDT (San Jose, Calif.). Double-stranded RNAs were prepared by annealing the two RNA strands in 2.5×PBS solutions. siRNAs were transfected into cells with lipid RNAiMAX (Life Technologies) as previously described (Hu et al., 2010). Cells were plated at a density of 80,000 per well of a 6-well plate 48 h before transfection for qPCR analysis. Cells were typically harvested 2 days after transfection.

qPCR Analysis.

C9orf72 expression was analyzed by quantitative PCR on a 7500 real-time PCR system (Applied Biosystems) using iTaq SYBR Green Supermix (Bio-rad). Data was normalized relative to levels of GAPDH mRNA. Primers specific for C9orf72 mRNA all three variants are as follows: F 5'-AGAAGGCACAGAGAGAATGGAA-3' (SEQ ID NO: 49); R 5'-TCATCATCATTGAGTACTGTATCAGC-3' (SEQ ID NO: 50). Primers for C9orf72 intron1: F 5'-ACGCCTGCACAATTTCAGCCCAA-3' (SEQ ID NO: 51); R 5'-CAAGTCTGTGTCATCTCGGAGCTG-3' (SEQ ID NO: 52). Primers for GAPDH: F 5'-GTCATCAATGGAAATCCCATCAC-3' (SEQ ID NO: 53); R 5'-TTCTCCATGGTGGTGAAGAC-3' (SEQ ID NO: 54).

RNA Immunoprecipitation (RIP).

RNA immunoprecipitation was performed as previously described using anti-AGO2 antibody (015-22031, Wako) (Hu et al., 2012). The enrichment of C9orf72 intron1 levels were quantified by qPCR.

RNA FISH and Imaging.

RNA fluorescent in situ hybridization (FISH) was performed following a Biosearch protocol with minor modification. Fibroblast cells were plated at a density of 10,000/well into Lab-Tek 8-well chambered cover glass slides. After one day, siRNA/lipid complex were added at 50 nM final concentration. 48 hrs after transfection, cells were fixed with 4% formaldehyde in 1×PBS and permeabilized in 70% ethanol at 4° C. overnight. Cells were washed with Wash Buffer (10% formamide in 2×SSC) for 5 minutes, and then incubated with pre-hybridization buffer (40% formamide in 2×SSC) at 60° C. for 20 mins. A $(CCCCGG)_4$-Cy3 DNA probe or a $(GGGGCC)_{3.3}$-Cy3 probe in Hybridization Buffer (100 mg/mL dextran sulfate and 40% formamide in 2×SSC) was added. The slide was placed in a humidified chamber and incubated in the dark at 37° C. overnight. On the next day, cells were washed twice with Wash Buffer at 37° C., and then stained with mounting media with DAPI (Vector Labs, H-1500).

Cells were imaged at 60× magnification using a Widefield Deltavision microscope. Images were processed by blind deconvolution with AutoQuant X3. Visualization of RNA foci were made using ImageJ. For quantification, at least 20 pictures were taken from randomly chosen microscopic fields, containing 100-300 cells for each treatment. Counting of foci was performed by different investigators. All data were generated by at least three independent experiments.

Example 2—Results and Discussion

Engineering Duplex RNAs to Recognize C/G-Rich Sequences.

Duplex RNAs intended for gene silencing consist of a guide strand complementary to the target RNA and a passenger strand that is complementary to the guide strand. Because duplex RNAs have two strands, a single duplex RNA has the capacity to recognize a sequence within an mRNA and a sequence within a corresponding antisense transcript. The challenge for recognition of GGGGCC/CCCCGG repeats is the likelihood that a C/G duplex will be unable to enter the RNAi induced silencing complex (RISC) because the parent duplex will be too stable.

AGO2 is the catalytic engine of RNAi (Liu, 2004) that drives cleavage of target RNAs when sequences are fully complementary. AGO2 can, however, also promote recognition of mismatched sequences. For example, microRNAs (miRNAs) that occur naturally supply an endogenous gene silencing mechanism that typically involves duplex RNAs that are mismatched relative to their mRNA targets. The introduction of mismatches into the central region of the RNA duplex eliminates the potential for substrate cleavage by AGO2 while continuing to permit the guide RNA strand to recognize the target site (Wang, 2008).

The inventors previously tested duplex anti-CAG RNAs with central mismatches as inhibitors of huntingtin, ataxin-3, and atrophin-1 expression (Hu et al., 2014). They found that these duplexes do not promote cleavage of their targets but can be potent and allele-selective inhibitors of protein expression. They reasoned that the introduction of central mismatches into the C/G-rich duplex RNA would reduce the affinity of the RNA duplex, increase the potential for the two strands to dissociate from one another, and make it more likely that the strands could enter into a complex with AGO2.

Duplex RNAs Inhibit GGGGCC and CCCCGG Foci.

The inventors tested the ability of RNA duplexes (Table 1) to inhibit foci. Duplex RNA R1 (R=Repeat targeted) was fully complementary to the C/G rich repeat. All other duplex RNAs contained A or U substitutions. RNA R1 has a measured melting temperature ($T_m$) of >87° C. Some modified RNAs with two, three, or four mismatches also had $T_m$ values >87° C. RNAs with more than four mismatches had $T_m$ values as low as 70.8° C. RNAs C1-C6 (C=control) were mismatched within their critical "seed" regions (bases 2-8) or scrambled duplexes. RNA E1 (E=exonic) was fully complementary to exon 4 and was used as a positive control for transfection efficiency.

The inventors introduced anti-GGGGCC/CCCCGG duplex RNAs (FIG. 1A, Table 1) into patient derived ALS patient-derived fibroblast cells by transfection with cationic lipid. Two days after transfection the inventors used fluorescent in situ hybridization (FISH) followed by analysis using fluorescent microscopy to monitor both CCCCGG and GGGGCC foci (FIG. 1B). Hundreds of cells were analyzed for each treatment to permit accurate quantitation of the number of cells containing at least one foci and the number of foci per one hundred cells.

After establishing the FISH detection assay, the inventors tested duplex RNAs for their ability to affect foci. Fully complementary duplex RNA R1 did not affect the total number of cells containing GGGGCC foci nor did they reduce the number of foci per cell (FIG. 2A). This result is consistent with the expectation that an entirely C/G duplex would be too stable to enter the RISC complex. Duplex R2, which contained two A/U substitutions, also did not significantly affect foci.

The inventors hypothesized that two mismatches may have been insufficient and tested duplexes with three to six mismatches relative to the target G-rich strand. Duplexes R3, R4, R5, and R6 reduced the number of cells with GGGGCC foci and the number of foci per one hundred cells, demonstrating the potential for duplexes to inhibit foci (FIGS. 2A-B). Duplex R7 with six mismatches relative to the target G-rich strand did not significantly inhibit foci, suggesting a limit to the number of substitutions that could be tolerated.

The inventors also tested duplexes R1, R3, and R4 for inhibition of foci formed by the C-rich antisense transcript. Similar to the outcome the inventors had observed for the G-rich strand, complementary duplex R1 did not reduce foci detection (FIG. 2C). Duplexes R3 and R4 both reduced the total number of cells with C-rich foci and the number of foci per cell (FIG. 2CD). For duplexes R1-R7, the inventors had introduced a 3' U substitution into the 3' sense strand to bias loading toward the antisense strand (Schwarz et al., 2003; Malefyt et al., 2014). Duplexes R3 and R4 that contained this substitution inhibited both the G-rich and C-rich foci. It is possible that standard rules for optimizing RNA duplexes are less powerful in the context of atypical C/G rich duplexes.

After demonstrating inhibition of both G-rich and C-rich foci by duplex RNAs, the inventors tested whether it would be possible to improve potency by redesigning the RNA sequences. They evaluated the effect of adding mismatches outside the central region of the duplex (Table 1). Duplexes R8, R9, R10, and R11 were all potent inhibitors of G-rich foci formation (FIG. 3A). They also examined duplexes R12, R13, and R14 that preserved seed sequence complementarity towards the C-rich sequence. R13 and R14 also had a 3' U substitution to bias loading recognition toward the C-rich target. The inventors found that each of these RNAs were effective inhibitors of C-rich foci (FIG. 3B).

To further evaluate inhibition of foci by RNA duplexes, the inventors examined inhibition as a function of time. Significant reductions in sense G-rich and antisense C-rich foci were observed 8-12 days after transfection (FIG. 3C). The fibroblast cells divide every 2-3 days and reduced efficacy is similar to that typically observed in the inventors' laboratory when using duplex RNAs.

Efficient gene silencing by duplex RNAs requires complementarity between the guide strand and the RNA target at bases 2 through 8, a region known as the seed sequence. To begin to test the mechanism of anti-GGGGCC/CCCCGG duplex RNAs, the inventors introduced mismatches into the seed sequence. They tested non-complementary control RNAs C1, C7 and C8, seed mismatched RNAs C2, C3, C5, C6, and scrambled duplex C4. The inventors observed duplexes with altered seed sequences did not inhibit sense or antisense foci (FIGS. 4A-B). Preventing foci inhibition by disrupting seed sequence complementarity is consistent with function through the RNAi machinery. They tested other noncomplementary or scrambled duplex RNAs and these also did not affect foci formation, also consistent with inhibition being an "on-target" effect through direct Watson-Crick interaction with the expanded GGGGCC or CCCCGG targets.

Because AGO2 is a key component in RNAi (Liu et al., 2004), the inventors used RNA immunoprecipitation (RIP) to determine whether their repeat-targeted RNAs were recruiting AGO2 for recognition of GGGGCC repeats within C9orf72 intronic RNA. Their RIP experiment employed an antibody that recognizes endogenously expressed AGO2 and detection employed PCR primers designed to amplify intron 1 RNA downstream from the GGGGCC repeat. RIP revealed that addition of RNA R3 promoted association of AGO2 with intronic C9orf72 RNA (FIG. 4CD). Sequencing confirmed that the RIP product was derived from C9orf72 intronic RNA (FIG. 4E).

Introduction of central mismatches relative to a target RNA is predicted to eliminate cleavage by AGO2 (Wang et al., 2008). To determine the effect of these mismatches on C9orf72 mRNA and intron 1 RNA, the inventors examined transcript levels by quantitative PCR. Levels of both the mRNA (FIG. 4F) and intron 1 RNA (FIG. 4G) were unchanged after treatment with various mismatch-containing repeat-targeted duplex RNAs. By contrast, fully complementary positive control duplex E1 efficiently silenced C9orf72 expression. These results are consistent with a mechanism of action that does not require slicer activity. RNA levels remain constant, and inhibition of foci is most likely due to binding of the RNA duplexes to the C-rich or G-rich transcripts.

The discovery of a linkage between the GGGGCC repeat expansion within intronic C9orf72 RNA and ALS/FTD was important because it is the most common inherited marker for these two diseases. There are currently no curative treatments for either disease, and agents that could slow disease progress would help satisfy a major unmet medical need. Application of anti-GGGGCC or anti-CCCCGG RNAs reduced detection of RNA foci by 40-60%. The sense and antisense transcripts derived from the mutant expanded hexanucleotide repeat have the potential to contribute to disease. These data suggest that duplex RNAs can be designed such that a single RNA can block both strands.

RNAi is a commonly used technique, but highly C/G rich sequences are often thought to be off-limits because of the high stability of structure formation. These results demonstrate that sequences that are entirely composed of C and G can be recognized by manipulating the presence of mismatched bases to tailor affinity. This finding widens the pool of cellular RNA sequences that can be accessed by RNAi and increases the potential to control gene expression. C9orf72 foci are located in human cell nuclei, and their inhibition by duplex RNAs provides another example of the power of nuclear RNAi to control gene expression.

TABLE 1 siRNAs targeting the hexanucleotide repeat

| No. | Sequence (AS, 5'-3, S, 3'-5') | SEQ ID NO: | Mismatch to repeat | Duplex Tm (° C.) | %Inhibition G-rich foci | %Inhibition C-rich foci |
|---|---|---|---|---|---|---|
| R1 | CGGCCCCGGCCCCGGCCCCdTdT (AS)<br>dTdTGCCGGGGCCGGGGCCGGGG (S) | 25<br>26 | 0 | >87 | N.I. | 8 |
| R2 | CGGCCCCGGAACCGGCCCCdTdT (AS)<br>dTdTGCCGGGGCCUUGGCCGGGG (S) | 27<br>28 | 10,11 | >87 | 18 | — |
| R3 | CGGCCCCGAAACCGGCCCCdTdT (AS)<br>dTdTUCCGGGGCUUUGGCCGGGG (S) | 1<br>2 | 9,10,11 | >87 | 73 | 58 |
| R4 | CGGCCCCGAAAACGGCCCCdTdT (AS)<br>dTdTUCCGGGGCUUUUGCCGGGG (S) | 3<br>4 | 9,10,11,12 | >87 | 52 | 48 |
| R5 | CGGCCCCAAAAACGGCCCCdTdT (AS)<br>dTdTUCCGGGGCUUUUGCCGGGG (S) | 5<br>6 | 8,9,10,11,12 | 83.7 | 43 | — |
| R6 | CGGCCCCGAAAACGACCCCdTdT (AS)<br>dTdTUCCGGGGCUUUUGCCGGGG (S) | 7<br>8 | 9,10,11,12,15 | 83.1 | 54 | — |
| R7 | CGGCCCCGAAAACGACCACdTdT (AS)<br>dTdTUCCGGGGCUUUUGCCGGGG (S) | 9<br>10 | 9,10,11,12,15,18 | 76.2 | 32 | — |
| R8 | CGGCCCCGAACCAGGACCCCdTdT (AS)<br>dTdTUCCGGGGCUUGGUCCUGGG (S) | 11<br>12 | 9,10,13,16 (AS) | >87 | 65 | — |
| R9 | CGGCCCCGAACCAGACCCCdTdT (AS)<br>dTdTUCCGGGGCUUGGUCCUGGG (S) | 13<br>14 | 9,10,13,15 (AS) | 84.0 | 78 | — |
| R10 | CGGCCCCGAAACCGACCCCdTdT (AS)<br>dTdTUCCGGGGCUUUGGCCGGGG (S) | 15<br>16 | 9,10,11,15 (AS) | 86.7 | 72 | — |
| R11 | CGGCCCCGAACCCGACCCCdTdT (AS)<br>dTdTUCCGGGGCUUGGGCUGGGG (S) | 17<br>18 | 9,10,15 (AS) | >87 | 55 | — |
| R12 | CGGCCCCGAAACCGACCCCdTdT (AS)<br>dTdTUCCGAGGCUUUGGCCGGGG (S) | 19<br>20 | 9,10,11,15,19 (S) | 77.3 | — | 62 |
| R13 | CGGCCCCGAAACCGGCCCUdTdT (AS)<br>dTdTGCCGAGGCUUUGGCCGGGG (S) | 21<br>22 | 9,10,11,15 (S) | 84.3 | — | 45 |
| R14 | CGGCCCCGAACCGGCCCUdTdT (AS)<br>dTdTGCCGAGACCUUGGCCGGGG (S) | 23<br>24 | 9,10,13,15 (S) | 70.8 | — | 46 |

Control siRNA

| | | | | | | |
|---|---|---|---|---|---|---|
| C1 | GCUAUACCAGCGUCGUCAUdTdT (AS)<br>dTdCGAUAUGGUCGCAGCAGUA (S) | 29<br>30 | — | — | N.I. | N.I. |
| C2 | ▶ CGGAAACGGCCCCGGCCCCdTdT (AS)<br>dTdTGCCUUUGCCGGGGCCGGGG (S) | 31<br>32 | 4,5,6 (AS)<br>Seed mismatch | >87 | N.I. | — |
| C3 | ▶ CGGACACGAAACCGCCCCdTdT (AS)<br>dTdTUCCUGUGCUUUGGCCGGGG (S) | 33<br>34 | 4,6,9,10,11 (AS)<br>Seed mismatch | >87 | N.I. | — |

TABLE 1-continued siRNAs targeting the hexanucleotide repeat

| No. | Sequence (AS, 5'-3, S, 3'-5') | SEQ ID NO: | Mismatch to repeat | Duplex Tm (° C.) | %Inhibition G-rich foci | %Inhibition C-rich foci |
|---|---|---|---|---|---|---|
| C4 | ▶ CCGCCGGGAAACGGCCCGGdTdT (AS)<br>dTdTUGCGGCCCUUUGCGGGCC (S) | 35<br>36 | 9,10,11 (AS)<br>Scrambled/mismatch | >87 | N.I. | — |
| C5 | CGGCCCCGGCCCCAAACCCdTdT (AS)<br>dTdTGCCGGGGCCGGGGUUUGGG (S) ◀ | 37<br>38 | 4,5,6 (S)<br>Seed mismatch | >87 | — | N.I. |
| C6 | CGGCCACGAACCCAAACCCdTdT (AS)<br>dTdTGCCGGGGCCGGGGUUUGGG (S) ◀ | 39<br>40 | 4,5,6 (S)<br>Seed mismatch | 71.9 | — | N.I. |
| C7 | GCAGCUGUUGCUACUGUUGdTdT (AS)<br>dTdTCGUCGACAACGAUGACAAC (S) | 41<br>42 | — | — | N.I. | N.I. |
| C8 | CAGACAAUGAUUCACACGGdTdT (AS)<br>dTdTGUCUGUUACUAAGUGUGCC (S) | 43<br>44 | — | — | N.I. | N.I. |

Bases that are mismatched relative to the GGGGCC/CCCCGG repeat are bolded and underlined.
N.I.: No significant inhibition detected;
(—): Not measured.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

X. References

The following references, to the extent that they provide exemplary procedural or other details supplementary to those set forth herein, are specifically incorporated herein by reference.

DeJesus-Hernandez et al., Neuron, 72, 245-256, 2012.
Donnelly et al., Neuron, 80, 415-428, 2013.
Fiszer et al., Nucleic Acids Res., 39, 5578-5585, 2011.
Gendron et al., Acta Neuropathol., 126, 839-844, 2013.
Haeusler et al., Nature, 507, 195-200, 2014.
Hu et al., Biochemistry, 53, 4510-4518, 2014.
Hu et al., Chem. Biol., 17, 1183-1188, 2010.
Hu et al., Nucl. Acids Res., 40, 11270-11280, 2012.
Lagier-Tourenne et al., Proc. Natl. Acad. Sci. USA, 110, E4530-E4539, 2013.
Lee et al., Cell, 5, 1178-1186, 2013.
Lima, et al., Cell 150, 883-894, 2012.
Ling et al., Neuron, 79, 416-438, 2013.
Liu et al., Science, 305, 1437-1441, 2004.
PCT International Applications Nos. PCT/US2008/066154.
PCT International Applications Nos. PCT/US2008/068922.
PCT International Applications Nos. PCT/US2008/064591.
Petri and Meister, Methods Mol. Biol., 986, 59-71, 2013.
Renton et al., Neuron, 72, 257-268, 2011.
Sareen et al., Sci. Trans. Med., 5, 208ra149, 2013.
Schwarz et al., Cell, 115, 119-208, 2003.
Szoka and Papahadjopoulos, Proc Natl Acad Sci USA, September; 75(9):4194-8, 1978.
U.S. Pat. No. 3,687,808
U.S. Pat. No. 4,587,044
U.S. Pat. No. 4,605,735
U.S. Pat. No. 4,667,025
U.S. Pat. No. 4,762,779
U.S. Pat. No. 4,789,737
U.S. Pat. No. 4,824,941
U.S. Pat. No. 4,828,979
U.S. Pat. No. 4,835,263
U.S. Pat. No. 4,845,205
U.S. Pat. No. 4,876,335
U.S. Pat. No. 4,904,582
U.S. Pat. No. 4,948,882
U.S. Pat. No. 4,958,013
U.S. Pat. No. 5,082,830
U.S. Pat. No. 5,109,124
U.S. Pat. No. 5,112,963
U.S. Pat. No. 5,118,802
U.S. Pat. No. 5,130,302
U.S. Pat. No. 5,134,066
U.S. Pat. No. 5,138,045
U.S. Pat. No. 5,175,273
U.S. Pat. No. 5,214,136
U.S. Pat. No. 5,214,136
U.S. Pat. No. 5,218,105
U.S. Pat. No. 5,245,022
U.S. Pat. No. 5,254,469
U.S. Pat. No. 5,258,506
U.S. Pat. No. 5,262,536
U.S. Pat. No. 5,272,250
U.S. Pat. No. 5,292,873
U.S. Pat. No. 5,317,098
U.S. Pat. No. 5,367,066
U.S. Pat. No. 5,371,241
U.S. Pat. No. 5,391,723
U.S. Pat. No. 5,414,077
U.S. Pat. No. 5,416,203
U.S. Pat. No. 5,432,272
U.S. Pat. No. 5,451,463
U.S. Pat. No. 5,457,187
U.S. Pat. No. 5,459,255
U.S. Pat. No. 5,484,908

U.S. Pat. No. 5,486,603
U.S. Pat. No. 5,502,177
U.S. Pat. No. 5,510,475
U.S. Pat. No. 5,512,439
U.S. Pat. No. 5,512,667
U.S. Pat. No. 5,514,785
U.S. Pat. No. 5,525,465
U.S. Pat. No. 5,525,711
U.S. Pat. No. 5,541,313
U.S. Pat. No. 5,545,730
U.S. Pat. No. 5,552,538
U.S. Pat. No. 5,552,540
U.S. Pat. No. 5,565,552
U.S. Pat. No. 5,567,810
U.S. Pat. No. 5,574,142
U.S. Pat. No. 5,578,717
U.S. Pat. No. 5,578,718
U.S. Pat. No. 5,580,731
U.S. Pat. No. 5,585,481
U.S. Pat. No. 5,587,371
U.S. Pat. No. 5,587,469
U.S. Pat. No. 5,591,584
U.S. Pat. No. 5,594,121
U.S. Pat. No. 5,595,726
U.S. Pat. No. 5,596,091
U.S. Pat. No. 5,597,696
U.S. Pat. No. 5,599,923
U.S. Pat. No. 5,599,928
U.S. Pat. No. 5,608,046
U.S. Pat. No. 5,614,617
U.S. Pat. No. 5,645,985
U.S. Pat. No. 5,681,941
U.S. Pat. No. 5,688,941
U.S. Pat. No. 5,750,692
U.S. Pat. No. 5,763,588
U.S. Pat. No. 5,830,653
U.S. Pat. No. 6,005,096
U.S. Pat. No. 6,268,490
U.S. Pat. No. 6,525,191
U.S. Pat. No. 6,670,461
U.S. Pat. No. 6,770,748
U.S. Pat. No. 6,794,499
U.S. Pat. No. 7,034,133
U.S. Pat. No. 7,053,207
U.S. Pat. No. 7,399,845
U.S. Patent Publication No. US2007/0287831.
U.S. Patent Publication No. US2008/0039618.
U.S. Patent Publication No. US2004/0171570.
U.S. Ser. No. 12/129,154.
U.S. Ser. No. 60/989,574.
U.S. Ser. No. 61/026,995.
U.S. Ser. No. 61/026,998.
U.S. Ser. No. 61/056,564.
U.S. Ser. No. 61/086,231.
U.S. Ser. No. 61/097,787.
U.S. Ser. No. 61/099,844.
Wang et al., *Nature,* 456, 921-926, 2008.
Wheeler et al., *Science,* 325, 336-339, 2009.
WO 1994/14226.
WO 2004/106356.
WO 2005/021570.
WO 2007/134181.

---

What is claimed is:

1. A double-stranded oligonucleotide of 18 to 22 nucleobases in length targeting a GGGGCC expanded repeat region in an intron of C9orf72, comprises (a) 3-5 central mismatches (within bases 9-14) within a target sequence comprising said expanded repeat sequence, or (b) 3-5 mismatches outside of the seed sequence (bases 2-8 within the guide strand complementary to the expanded repeat sequence).

2. The double-stranded oligonucleotide of claim 1, wherein said oligonucleotide comprises one or more chemically-modified nucleobases.

3. The double-stranded oligonucleotide of claim 2, wherein said one or more chemically-modified nucleobases is a nuclease-resistant modification.

4. The double-stranded oligonucleotide of claim 3, wherein said nuclease-resistant modification is a modified sugar moiety or a modified internucleoside linkage.

5. The double-stranded oligonucleotide of claim 4, wherein said modified sugar moiety is a high-affinity sugar modification.

6. The double-stranded oligonucleotide of claim 5, wherein the high-affinity sugar modification is a bicyclic sugar moiety, or a 2'-modified sugar moiety.

7. The double-stranded oligonucleotide of claim 4, wherein the modified sugar moiety is a 4' to 2' bicyclic sugar moiety.

8. The double-stranded oligonucleotide of claim 1, wherein said double-stranded oligonucleotide comprises terminal dT residues.

9. The double-stranded oligonucleotide of claim 1, wherein said double-stranded oligonucleotide comprises 3' and/or '5 2'-O-methyl modifications.

10. The double-stranded oligonucleotide of claim 1, wherein the nucleobases are linked by phosphate internucleoside linkages.

11. The double-stranded oligonucleotide of claim 1, wherein said double-stranded oligonucleotide comprises DNA nucleobases, RNA nucleobases or a mixture of DNA and RNA nucleobases.

12. The double-stranded oligonucleotide of claim 1, wherein said double-stranded oligonucleotide is selected from the following RNAs, or a DNA cognate thereof:

```
CGGCCCCGAAACCGGCCCCdTdT (AS)   SEQ ID NO: 1
dTdTUCCGGGGCUUUGGCCGGGG (S)    SEQ ID NO: 2

CGGCCCCGAAAACGGCCCCdTdT (AS)   SEQ ID NO: 3
dTdTUCCGGGGCUUUUGCCGGGG (S)    SEQ ID NO: 4

CGGCCCCAAAAACGGCCCCdTdT (AS)   SEQ ID NO: 5
dTdTUCCGGGGCUUUUGCCGGGG (S)    SEQ ID NO: 6

CGGCCCCGAAAACGACCCCdTdT (AS)   SEQ ID NO: 7
dTdTUCCGGGGCUUUUGCCGGGG (S)    SEQ ID NO: 8

CGGCCCCGAAAACGACCACdTdT (AS)   SEQ ID NO: 9
dTdTUCCGGGGCUUUUGCCGGGG (S)    SEQ ID NO: 10

CGGCCCCGAACCAGGACCCdTdT (AS)   SEQ ID NO: 11
dTdTUCCGGGGCUUGGUCCUGGG (S)    SEQ ID NO: 12

CGGCCCCGAACCAGACCCCdTdT (AS)   SEQ ID NO: 13
dTdTUCCGGGGCUUGGUCCUGGG (S)    SEQ ID NO: 14

CGGCCCCGAAACCGACCCCdTdT (AS)   SEQ ID NO: 15
dTdTUCCGGGGCUUUGGCCGGGG (S)    SEQ ID NO: 16

CGGCCCCGAACCCGACCCCdTdT (AS)   SEQ ID NO: 17
dTdTUCCGGGGCUUGGGCUGGGG (S)    SEQ ID NO: 18

CGGCCCCGAAACCGACCCCdTdT (AS)   SEQ ID NO: 19
dTdTUCCGAGGCUUUGGCCGGGG (S)    SEQ ID NO: 20

CGGCCCCGAAACCGGCCCUdTdT (AS)   SEQ ID NO: 21
dTdTGCCGAGGCUUUGGCCGGGG (S)    SEQ ID NO: 22

CGGCCCCGAAACCGGCCCUdTdT (AS)   SEQ ID NO: 23
dTdTGCCGAGACCUUGGCCGGGG (S)    SEQ ID NO: 24.
```

13. The double-stranded oligonucleotide of claim 1, wherein said central mismatches comprise one or more abasic or unlocked nucleotides.

14. A method of selectively decreasing the expression of C9orf72 transcripts in a cell having an expanded GGGGCC repeat in an intron of C9orf72 comprising contacting the cell with a double-stranded oligonucleotide of 13 to 22 nucleobases in length targeting a GGGGCC expanded repeat region in an intron of C9orf72, comprises (a) 3-5 central mismatches (within bases 9-14) within a target sequence comprising said expanded repeat sequence, or (b) 3-5 mismatches outside of the seed sequence (bases 2-8 within the guide strand complementary to the expanded repeat sequence).

15. The method of claim 14, wherein the expanded GGGGCC repeat region contains 500 or more repeats.

16. The method of claim 14, wherein the expanded GAA repeat region contains about 700 to 1600 repeats.

17. The method of claim 14, where said cell is contacted with said double-stranded oligonucleotide at about 5-75 nM.

18. The method of claim 14, wherein the cell is located in a subject suffering from a GGGGCC repeat disease.

19. The method of claim 18, wherein contacting comprises administering said double-stranded oligonucleotide by direct administration into the central nervous system, cerebrospinal fluid, or mediated uptake across the blood brain barriers, and/or administering said double-stranded oligonucleotide more than once.

20. The method of claim 18, further comprising administering a second therapeutic agent to said subject.

21. The method of claim 18, wherein said subject has or exhibits a symptom of amyotrophic lateral sclerosis (ALS) and frontotemporal dementia (FTD).

22. The method of claim 21, wherein ALS/FTD foci in the brain tissue of said subject are reduced in number or size.

* * * * *

UNITED STATES PATENT AND TRADEMARK OFFICE
CERTIFICATE OF CORRECTION

PATENT NO. : 10,538,762 B2
APPLICATION NO. : 15/518824
DATED : January 21, 2020
INVENTOR(S) : David Corey et al.

Page 1 of 1

It is certified that error appears in the above-identified patent and that said Letters Patent is hereby corrected as shown below:

In the Specification

In Column 1, Lines 12-15, delete paragraph and insert:
--This invention was made with government support under grant numbers GM106151 and GM073042 awarded by The National Institutes of Health. The government has certain rights in the invention.--
therefor.

Signed and Sealed this
Thirtieth Day of June, 2020

Andrei Iancu
*Director of the United States Patent and Trademark Office*

SEQUENCE LISTING

<160> NUMBER OF SEQ ID NOS: 54

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
cggccccgaa accggcccct t                                              21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2 ttccggggc uuuggccggg g                                               21

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
cggccccgaa aacggcccct t                                              21

-continued

```
<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4 ttccggggc uuugccggg g                                                     21

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
cggccccaaa aacggcccct t                                                   21

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6 ttccggggc uuugccggg g                                                     21

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
cggccccgaa aacgacccct t                                                   21

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8 ttccggggc uuugccggg g                                                     21

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
cggccccgaa aacgaccact t                                                   21

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide
```

```
<400> SEQUENCE: 10
ttuccggggc uuuugccggg g                                              21

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
cggccccgaa ccaggaccct t                                              21

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
ttuccggggc uugguccugg g                                              21

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
cggccccgaa ccagacccct t                                              21

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 14
ttuccggggc uugguccugg g                                              21

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15
cggccccgaa accgacccct t                                              21

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 16
ttuccggggc uuuggccggg g                                              21

<210> SEQ ID NO 17
<211> LENGTH: 21
```

<212> TYPE: DNA
<213> ORGANISM: Artificial sequence
<220> FEATURE:
<223> OTHER INFORMATION: Synthetic oligonucleotide

<400> SEQUENCE: 17
cggccccgaa cccgacccct t                                              21

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
ttuccggggc uugggcuggg g                                              21

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
cggccccgaa accgacccct t                                              21

<210> SEQ ID NO 20
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 20
ttuccgaggc uuuggccggg g                                              21

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
cggccccgaa accggcccut t                                              21

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
ttgccgaggc uuuggccggg g                                              21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23

```
cggccccgaa accggcccut t                                              21
```

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24

```
ttgccgagac cuuggccggg g                                              21
```

<210> SEQ ID NO 25
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 25

```
cggccccggc cccggcccct t                                              21
```

<210> SEQ ID NO 26
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 26

```
ttgccggggc cggggccggg g                                              21
```

<210> SEQ ID NO 27
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 27

```
cggccccgga accggcccct t                                              21
```

<210> SEQ ID NO 28
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 28

```
ttgccggggc cuuggccggg g                                              21
```

<210> SEQ ID NO 29
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 29

```
gcuauaccag cgucgucaut t                                              21
```

<210> SEQ ID NO 30
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 30
ttcgauaugg ucgcagcagu a             21

<210> SEQ ID NO 31
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 31
cggaaacggc cccggcccct t             21

<210> SEQ ID NO 32
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 32
ttgccuuugc cggggccggg g             21

<210> SEQ ID NO 33
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 33
cggacacgaa accggcccct t             21

<210> SEQ ID NO 34
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 34
ttuccugugc uuuggccggg g             21

<210> SEQ ID NO 35
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 35
ccgccgggaa acggcccggt t             21

<210> SEQ ID NO 36
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 36
ttugcggccc uuugccgggc c             21

<210> SEQ ID NO 37
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 37
cggccccggc cccaaaccct t                                      21

<210> SEQ ID NO 38
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 38
ttgccggggc cgggguuugg g                                      21

<210> SEQ ID NO 39
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 39
cggccacgaa cccaaaccct t                                      21

<210> SEQ ID NO 40
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 40
ttgccggggc cgggguuugg g                                      21

<210> SEQ ID NO 41
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 41
gcagcuguug cuacuguugt t                                      21

<210> SEQ ID NO 42
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 42
ttcgucgaca acgaugacaa c                                      21

<210> SEQ ID NO 43
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 43
cagacaauga uucacacggt t　　　　　　　　　　　　　　　　　　　21

<210> SEQ ID NO 44
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 44
ttgucuguua cuaagugugc c　　　　　　　　　　　　　　　　　　　21

<210> SEQ ID NO 45
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 45
tcggtgtgct ccccattctg tgggacatga cctggttgct tcacagctcc gagatgacac    60
agact                                                               65

<210> SEQ ID NO 46
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 46
tcggtgtgct ccccattctg tgggacatga cctggttgct tcacagctcc gagatgacac    60
agact                                                               65

<210> SEQ ID NO 47
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 47
tcggtgtgct ccccattctg tgggacatga cctggttgct tcacagctcc gagatgacac    60
agact                                                               65

<210> SEQ ID NO 48
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 48
tcggtgtgct ccccattctg tgggacatga cctggttgct tcacagctcc gagatgacac    60
agact                                                               65

<210> SEQ ID NO 49
<211> LENGTH: 22
<212> TYPE: DNA
<213> ORGANISM: Artificial sequence
<220> FEATURE:

```
<223> OTHER INFORMATION: Synthetic primer

<400> SEQUENCE: 49
agaaggcaca gagagaatgg aa                                              22

<210> SEQ ID NO 50
<211> LENGTH: 26
<212> TYPE: DNA
<213> ORGANISM: Artificial sequence
<220> FEATURE:
<223> OTHER INFORMATION: Synthetic primer

<400> SEQUENCE: 50
tcatcatcat tgagtactgt atcagc                                          26

<210> SEQ ID NO 51
<211> LENGTH: 23
<212> TYPE: DNA
<213> ORGANISM: Artificial sequence
<220> FEATURE:
<223> OTHER INFORMATION: Synthetic primer

<400> SEQUENCE: 51
acgcctgcac aatttcagcc caa                                             23

<210> SEQ ID NO 52
<211> LENGTH: 24
<212> TYPE: DNA
<213> ORGANISM: Artificial sequence
<220> FEATURE:
<223> OTHER INFORMATION: Synthetic primer

<400> SEQUENCE: 52
caagtctgtg tcatctcgga gctg                                            24

<210> SEQ ID NO 53
<211> LENGTH: 23
<212> TYPE: DNA
<213> ORGANISM: Artificial sequence
<220> FEATURE:
<223> OTHER INFORMATION: Synthetic primer

<400> SEQUENCE: 53
gtcatcaatg gaaatcccat cac                                             23

<210> SEQ ID NO 54
<211> LENGTH: 20
<212> TYPE: DNA
<213> ORGANISM: Artificial sequence
<220> FEATURE:
<223> OTHER INFORMATION: Synthetic primer

<400> SEQUENCE: 54
ttctccatgg tggtgaagac                                                 20
```